(12) United States Patent
Zagury et al.

(10) Patent No.: US 7,314,629 B2
(45) Date of Patent: Jan. 1, 2008

(54) NON-IMMUNOSUPPRESSIVE IMMUNOGENIC OR VACCINE COMPOSITION COMPRISING A MUTATED E7 PROTEIN OF THE HPV-16 VIRUS

(75) Inventors: Daniel Zagury, Paris (FR); Hélène Le Buanec, Paris (FR); Bernard Bizzini, Albi (FR)

(73) Assignee: Neovacs, Paris (FR)

( * ) Notice: Subject to any disclaimer, the term of this patent is extended or adjusted under 35 U.S.C. 154(b) by 401 days.

(21) Appl. No.: 10/512,045

(22) PCT Filed: Apr. 4, 2003

(86) PCT No.: PCT/FR03/01082

§ 371 (c)(1),
(2), (4) Date: Oct. 21, 2004

(87) PCT Pub. No.: WO03/090667

PCT Pub. Date: Nov. 6, 2003

(65) Prior Publication Data

US 2006/0233820 A1     Oct. 19, 2006

(30) Foreign Application Priority Data

Apr. 24, 2002 (FR) .................................. 02 05173

(51) Int. Cl.
*A61K 39/12* (2006.01)
(52) U.S. Cl. .............................. 424/204.1; 424/130.1; 435/6
(58) Field of Classification Search ............. 424/204.1, 424/130.1; 435/6, 69.1, 91.1, 91.33
See application file for complete search history.

(56) References Cited

U.S. PATENT DOCUMENTS 6,235,523 B1    5/2001   Gajewczyk et al.

FOREIGN PATENT DOCUMENTS

| EP | 0 451 550 A | 10/1991 |
|---|---|---|
| FR | 2 794 371 | 12/2000 |
| WO | WO 96/19496 | 6/1996 |
| WO | WO 99 10375 | 3/1999 |
| WO | WO 01/14416 A2 | 3/2001 |

*Primary Examiner*—Ali R. Salimi
(74) *Attorney, Agent, or Firm*—Jacobson Holman PLLC

(57) ABSTRACT

The invention relates to an immunogenic or vaccine composition inducing an immune response towards the HPV-16 Papillomavirus native E7 protein, without simultaneously inducing an immunosuppression, said composition comprising, as the active ingredient, a non immunosuppressive mutated E7 protein, comprising the amino acid sequence consisting, from the N-terminal end to the C-terminal end, in:

i. the 1-19 amino acid sequence of sequence SEQ ID No. 3;
ii. an amino acid sequence possessing (a) the substitution of at least one amino acid, compared to the 20-29 corresponding amino acid sequence of sequence SEQ ID No. 3 or (b) the deletion of at least four consecutive amino acids, compared to the 20-29 corresponding amino acid sequence of sequence SEQ ID No. 3; and
iii. the 30-98 amino acid sequence of sequence SEQ ID No 3.

24 Claims, 13 Drawing Sheets

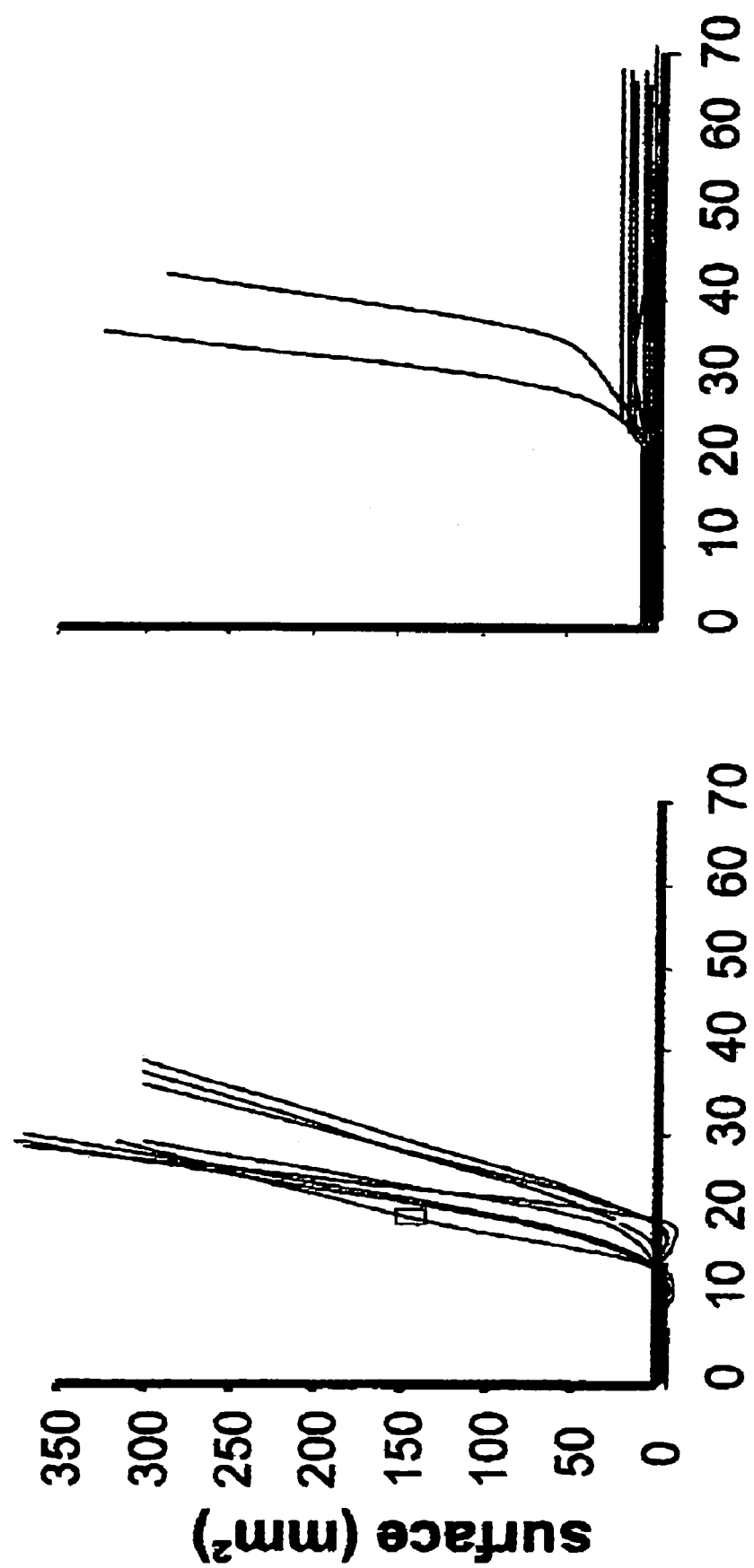

SEQUENCE LISTING

<160> NUMBER OF SEQ ID NOS: 4

<210> SEQ ID NO 1
<211> LENGTH: 92
<212> TYPE: PRT
<213> ORGANISM: artificial sequence
<220> FEATURE:
<223> OTHER INFORMATION: artificial sequence
      description: a mutated E7 protein
      of the HPV-16 virus: E7-delta-21-26

<400> SEQUENCE: 1

Met His Gly Asp Thr Pro Thr Leu His Glu Tyr Met Leu Asp Leu Gln
 1               5                  10                  15

Pro Glu Thr Thr Gln Leu Asn Asp Ser Ser Glu Glu Glu Asp Glu Ile
            20                  25                  30

Asp Gly Pro Ala Gly Gln Ala Glu Pro Asp Arg Ala His Tyr Asn Ile
        35                  40                  45

Val Thr Phe Cys Cys Lys Cys Asp Ser Thr Leu Arg Leu Cys Val Gln
    50                  55                  60

Ser Thr His Val Asp Ile Cys Thr Leu Glu Asp Leu Leu Met Gly Thr
65                  70                  75                  80

Leu Gly Ile Val Cys Pro Ile Cys Ser Arg Lys Pro
                85                  90

<210> SEQ ID NO 2
<211> LENGTH: 276
<212> TYPE: DNA
<213> ORGANISM: artificial sequence
<220> FEATURE:
<223> OTHER INFORMATION: artificial sequence
      description: a mutated E7 protein
      of the HPV-16 virus: E7-delta-21-26E7-delta-21-26

<400> SEQUENCE: 2
catggagata cacctacatt gcatgaatat atgttagatt tgcaaccaga gacaactcaa      60
ttaaatgaca gctcagagga ggaggatgaa atagatggtc cagctggaca agcagaaccg     120
gacagagccc attacaatat tgtaaccttt tgttgcaagt gtgactctac gcttcggttg     180
tgcgtacaaa gcacacacgt agacattcgt actttggaag acctgttaat gggcacacta     240
ggaattgtgt gccccatctg ttctcagaaa ccataa                               276

<210> SEQ ID NO 3
<211> LENGTH: 98
<212> TYPE: PRT
<213> ORGANISM: Human papillomavirus type 16

<400> SEQUENCE: 3

Met His Gly Asp Thr Pro Thr Leu His Glu Tyr Met Leu Asp Leu Gln
 1               5                  10                  15

Pro Glu Thr Thr Asp Leu Tyr Cys Tyr Glu Gln Leu Asn Asp Ser Ser

```
                         20                   25                      30
Glu Glu Glu Asp Glu Ile Asp Gly Pro Ala Gly Gln Ala Glu Pro Asp
             35                       40                  45

Arg Ala His Tyr Asn Ile Val Thr Phe Cys Cys Lys Cys Asp Ser Thr
         50                      55                  60

Leu Arg Leu Cys Val Gln Ser Thr His Val Asp Ile Cys Thr Leu Glu
 65                      70                  75                  80

Asp Leu Leu Met Gly Thr Leu Gly Ile Val Cys Pro Ile Cys Ser Arg
                 85                      90                  95

Lys Pro

<210> SEQ ID NO 4
<211> LENGTH: 294
<212> TYPE: DNA
<213> ORGANISM: Human papillomavirus type 16

<400> SEQUENCE: 4
catggagata cacctacatt gcatgaatat atgttagatt tgcaaccaga gacaactgat        60
ctctactgtt atgagcaatt aaatgacagc tcagaggagg aggatgaaat agatggtcca      120
gctggacaag cagaaccgga cagagcccat tacaatattg taacctttg ttgcaagtgt       180 gactctacgc ttcggttgtg cgtacaaagc acacacgtag acattcgtac tttggaagac     240
ctgttaatgg gcacactagg aattgtgtgc cccatctgtt ctcagaaacc ataa            294
```

NON-IMMUNOSUPPRESSIVE IMMUNOGENIC OR VACCINE COMPOSITION COMPRISING A MUTATED E7 PROTEIN OF THE HPV-16 VIRUS

This is a nationalization of PCT/FR03/01082 filed Apr. 4, 2003 and published in French.

1. Field of the Invention

The present invention relates to the field of the prevention or the treatment of some cancers associated with an infection through the HPV-16 type Papillomavirus.

2. Prior Art

Several human Papillomavirus species, or HPV, are considered today as causal agents for cancers. In particular, the 16, 18, 31, 33 and 51 type HPV are frequently associated with anogenital cancers, including woman's uterine neck cancer.

More than 50% of the squamous carcinomas in the uterine neck are associated with the HPV-16 type Papillomavirus.

The HPV E6 and E7 viral oncoproteins are strongly involved in the molecular mechanisms whereby such viruses contribute to the development of such cancers. Both oncoproteins act through inactivating the cellular cycle regulators formed by the p53 protein and the retinoblastoma protein, thereby causing the initiating event of the multiple step progression towards cancer.

Generally, malignant tumors consist in cancer cells bearing associated antigens (TAA) or specific antigens (TSA) and a particular stroma micro-environment, characterized by a hypervascularization, or neoangiogenesis, which might be coupled with a paralysis of the immune cells, i.e. in an immunosuppression state. Initially, immunosuppression remains located at the tumor level, as the individual is still able to defend himself against the other aggressions such as infections.

However, with the metastatic dissemination, immunosuppression may spread and become generalized, as evidenced by the vulnerability to infections of the cancerous patient with terminal cancer. Such an immunosuppression involves paralyzing factors being produced by cancerous cells or by cells from their environment. A local paralysis of the immune system cells, or immunosuppression, represents therefore a major weapon of cancerous cells that allows them to escape from the host's immune system.

Such an immunosuppression condition has also been observed in cancers caused by a HPV-16 infection. Such an immunosuppression is today a major technical obstacle in the development of preventive or curative vaccine compositions against cancers caused by a HPV-16 infection. In fact, the current anti-HPV-16 vaccine strategies favour the induction of a proliferation of cytotoxic T cells specifically recognizing some antigens produced by HPV-16, in particular E6 and E7 proteins, when associated with class I antigens of the histocompatibility major complex (MHC) at the membrane surface of infected cancerous cells.

Some authors have associated the immunosuppression observed in cancers caused by HPV-16 with the observation of reduced expression levels of the MHC class I molecules at the surface of cancerous cells of the uterine neck (Cruz et al., 1999), or also with a reduction of the expression of the delta chain of the T cells receptor (TCR) in patients expressing a pre-neoplastic dysplasia (Muderspach et al., 2000). Other authors have associated the immunosuppression condition with a lack of response from the T cells to possible signals produced by tumor cells and transmitted to immune cells, causing thereby their apoptosis, for example because of a Fas/Fas-ligand interaction (Schoell et al., 1999).

Others authors have observed that the immunosuppression associated with a cancer caused by a HPV infection is concomitant with an increase in IL-10 (El Sherif et al., 2001; Giannini et al. 1998; Giannini et al. 2002) and in TGF-beta-1 (Giannini et al. 1998), as well as with a decrease in the subepithelial IFN-gamma (El Sherif et al., 2001).

Prior works of the inventors disclosed in the International Application published under WO 00/03732 have shown that, in the case of the cancer of the uterine neck caused by HPV, the Papillomavirus E7 protein was involved in a local immunosuppression at the level of the tumors or infected cells.

The immunosuppression induced by E7 protein is characterized by the inhibition of the proliferation of T cells stimulated by PPD or the tetanus toxoid, the inhibition of the proliferation of T cells stimulated by allogenic cells, the α-IFN overproduction (immunosuppressive cytokine) by the cells presenting the antigen (APC). In order to decrease or block the immunosuppression induced by the HPV soluble E7 protein, it has been suggested to use non toxic derivatives of the E7 protein as the antigen for inducing the antibodies specifically directed against the extracellular E7 protein. In order to produce E7 derived immunogenic compounds without the deleterious effects of the native protein, it has been suggested to modify the native E7 protein either through a chemical modification or a genetic modification, including by producing insertions, deletions or substitutions of amino acid residues adapted for reducing or suppressing the deleterious functional sites of the native protein. In such a context, a chemically modified E7 protein has been disclosed, which lacks immunosuppressive activity, after the treatment of the native E7 protein by glutaraldehyde.

The chemical modification being suggested to reduce or block the immunosuppression properties of the native E7 protein, such as disclosed in the state of the art, aim at adding a chemical group to the carbon backbone of the native E7 protein, through coupling of a reactive function of one of the amino acids of such a protein with an aldehyde, carboxamide or maleimide function, without altering the amino acid sequence of the native protein, i.e., without bringing any significant modifications to the primary structure of the E7 protein.

In fact, the various anti-E7 immunogenic compositions as disclosed in the state of the art, in order to produce preventive or curative vaccine preparations against cancers due to a HPV-16 infection, predominantly aiming at inducing an immune response through the production of specific cytotoxic lymphocytes (CTL) for the E7 protein expressed at the surface of the infected cells, contain, as an antigen, either the full E7 protein, optionally chemically modified (Gerard et al., 2001) or peptides derived from the E7 protein (Muderspach et al., 2000; Schoell, 1999—see above). In all cases, including when the peptides derived from the native E7 protein are used, there is no modification introduced in the amino acid sequence of the native protein, and consequently, in the initial primary structure of amino acids. This is simply explained by the wish to keep intact the epitopes of interest in the native E7 protein in order to favour the induction of an immune response, in particular the production of CTL cells, capable to specifically and efficiently recognize the native E7 protein produced by the infected cells.

And even when rearranging the primary amino acid structure of the E7 protein is contemplated, with a view to the production of an immunogenic protein with reduced carcinogenic or transforming properties, the concern is to keep at least one full copy of the amino acid sequence of the E7 protein within the rearranged immunogenic compound, in order to keep present, within said immunogenic compound, all the native E7 protein potential epitopes.

Thus, Osen et al. (2001) have disclosed the building of a DNA encoding an immunogenic compound prone to induce the production of cytotoxic lymphocytes (CTL) specifically recognizing the native E7 protein expressed at the surface of HPV-16 infected cancerous cells, in an anti-HPV vaccine strategy with DNA, and not directly with a peptide immunogenic compound. To avoid any recombination event that could lead to the native E7 protein being overproduced, or at least a recombined protein with the carcinogenic properties of the native E7 protein, these authors have built a DNA encoding an immunogenic protein wherein all the epitopes of the native E7 protein are represented, although each of the peptide domains, respectively (i) domain 1-10, (ii) domain 11-40, (iii) domain 41-70 and (iv) domain 71-98, has been inverted into the final immunogenic peptide compound. Said authors insist on the need to produce an immunogenic peptide compound having kept all the potential CTL epitopes of the native E7 protein, while having simultaneously lost its cancerous transformation properties of the cells. Last, these authors further suggest increasing the innocuousness of the rearranged immunogenic peptide compound, with respect to the cancerogenic power thereof, suppressing thereby the binding domain of the native E7 protein with the retinoblastoma pRB protein, ranging from amino acid 21 to amino acid 26 of E7, responsible for the cancerigenic activity of the native E7 protein. However, such an embodiment of a non cancerigenic immunogenic peptide compound has not concretely been achieved.

DESCRIPTION OF THE INVENTION

Surprisingly, it has been currently shown according to the invention that there could be obtained, through a directed mutagenesis of the DNA encoding the native E7 protein, a mutated protein having an identical ability, even an improved ability, to induce a specific immune response to the native E7 protein, and wherein the immunosuppression properties of the native E7 protein have been blocked.

It has thus been shown for the first time according to the invention, surprisingly, that a peptide fragment located in the region from the amino acid in position 20 (Thr or T) up to the amino acid in position 29 (Asn or N) of the native E7 protein of the HPV-16 Papillomavirus was responsible for the immunosuppressive activity of said protein.

For the purpose of the present disclosure, a protein differing from at least one amino acid, compared to the HPV-16 native E7 protein with sequence SEQ ID No. 3, is referred to as a "mutated" E7 protein according to the invention, when the difference(s) in amino acids is or are located in the corresponding 20-29 peptide region of the native E7 protein of sequence SEQ ID No. 3.

In particular, it has been shown according to the invention that a mutated E7 protein comprising the substitution of at least one amino acid, preferably at least two amino acids, compared to sequence SEQ ID No. 3 of the native E7 protein, has lost its property to induce the immunosuppression that was previously reported for the native E7 protein. It has thus been shown that a mutated E7 protein comprising the substitution of the cysteine acid residue in position 24 by a glycine residue (CYS24GLY) and the substitution of the glutamic acid residue in position 26 by a glutamine residue (GLU26GLN), compared to sequence SEQ ID No. 3 of native E7 protein, has lost the immunosuppressive property of the native E7 protein. Likewise, it has been shown that a mutated E7 protein comprising the substitution of the cysteine residue in position 24 by a serine residue (CYS24SER) and the substitution of a glutamic acid residue in position 26 by a glutamine residue (GLU26GLN), compared to sequence SEQ ID No. 3 of the native E7 protein, has lost the native E7 protein immunosuppressive property.

It has also been shown according to the invention that a mutated E7 protein comprising, compared to the SEQ ID No. 3 amino acid sequence of native E7 protein, a deletion of at least four, and preferably one deletion of four, five, six, seven, eight, nine or ten consecutive amino acids in the corresponding polypeptide region of sequence SEQ ID No. 3 ranging from the amino acid in position 20 up to the amino acid in position 29, according to the sequence SEQ ID No. 3 numbering, has lost the immunosuppressive property observed for the native E7 protein.

In particular, it has been shown that the mutated E7 protein comprising the deletion of peptide fragment 21 (Asp or D) to 26 (Glu or E), according to the numbering of sequence SEQ ID No. 3, has lost the immunosuppressive property observed for the native E7 protein. The mutated E7 protein having its region corresponding to amino acids 21 to 26 of native E7 protein deleted is also called E7Δ21-26 protein for the purposes of the present specification.

As such, the E7Δ21-26 protein, produced by genetic recombination, has been disclosed by D'Anna et al. (2001, J. Natl. Cancer Inst. Vol. 93 (24):1843-1851).

Similarly, it has been shown that the mutated E7 protein comprising the deletion of peptide fragment 21 (Asp or D) to 25 (Tyr or Y), according to the numbering of sequence SEQ ID No. 3, has lost its immunosuppressive property observed for the native E7 protein. The mutated E7 protein having its region corresponding to amino acids 21 to 25 of the native E7 protein deleted is also called E7Δ21-25 protein for the purposes of the present specification.

It has thus been shown according to the invention that simple substitutions of amino acids in the 20-29 peptide region of the native E7 protein make it possible to block the immunosuppressive activity observed for such a protein. Thus, minor alterations of the primary structure of the native E7 protein, in the 20-29 peptide region, destroy the typical immunosuppressive properties for the native E7 protein.

According to the invention, a protein is "immunosuppressive" when such a protein inhibits by at least 60%, and preferably by at least 70%, the in vitro proliferation of mononucleated cells from the human peripheral blood of a subject vaccinated against tetanus (toxoid tetanus antigen) and/or diphtheria (antigen of the "tuberculin-Purified Protein Derivative" or "PPD" type), said proliferation of mononucleated cells being induced by pre-incubating such cells with (i) the PPD antigen, (ii) with the toxoid tetanus antigen, (iii) with an association of the PPD antigen and the toxoid tetanus antigen or also (iv) with allogenic cells compared to said mononucleated cells. In such test, the potentially immunosuppressive protein is used in the concentration inducing the maximum proliferation inhibition value, according to an effect-dose curve. Example 6 gives an illustration of such a test.

Also, a protein is "immunosuppressive" when such a protein induces an abnormal in vitro production level of immunosuppressive cytokines, respectively the IL-10 by mononucleated cells of the peripheral blood, and the α-IFN or IL-10 by the cells with the antigen (APC).

Moreover, as this will be further detailed hereinunder in the disclosure and as this is illustrated in the examples, the mutated E7 proteins hereinabove share in common, in addition to their non suppressive character, also the ability to stimulate the production of "neutralizing" antibodies towards the native E7 protein, i.e. the production of antibodies recognizing the native E7 protein and blocking the immunosuppressive activity of the native E7 protein, being deleterious for the cells of the immune system. According to the invention, an anti-E7 body is so-called "neutralizing", including when blocking the ability of the native E7 protein to stimulate the production of α-TNF by human macrophages pretreated by γ-IFN, according to the test further described in example 1.

These results made it possible to define a mutated E7 protein family which all share in common possessing mutations, substitution(s) or deletion of amino acids, compared to the amino acid sequence of the native E7 protein.

Generally speaking, it is meant under non immunosuppressive "mutated E7" protein according to the invention, a protein comprising the amino acid sequences consisting, from the N-terminal end to the C-terminal end, in:
  i. the 1-19 amino acid sequence of sequence SEQ ID No. 3;
  ii. an amino acid sequence possessing (a) the substitution of at least one, preferably at least two amino acids, compared to the corresponding 20-29 amino acid sequence of sequence SEQ ID No. 3 or (b) the deletion of at least four consecutive amino acids, compared to the corresponding 20-29 amino acid sequence of sequence SEQ ID No. 3; and
  iii. the 30-98 amino acid sequence of sequence SEQ ID No. 3.

According to the invention, a mutated E7 protein "comprising" the amino acid sequence as defined hereinabove is a protein, the amino acid sequence of which "essentially consists" in the above-mentioned amino acid sequence. In other words, a mutated E7 protein according to the invention might comprise, in addition to the above-mentioned amino acid sequence, also one or two additional amino acid sequences of at most 20, advantageously at most 15, preferably at most 10, and most preferably at most 6 amino acids, the additional amino acid sequence(s) being located respectively at the N-terminal end of region (i) or at the C-terminal end of region (ii), and in some cases both at the N-terminal end of region (i) and at the C-terminal end of region (ii). In the latter case, the additional sequence located at the N-terminal end of region (i) may be distinct from the additional sequence located at the C-terminal end, or on the opposite, both additional sequences may be identical. Generally, a mutated E7 protein according to the invention comprises, compared to the hereinabove amino acid sequence defining it, one single additional amino acid sequence, such as a poly(histidine) amino acid sequence, for example a sequence consisting in a six histidine residue polymer.

It results from the above-mentioned definition that a mutated E7 protein according to the invention has two amino acid regions identical to the corresponding peptide regions of sequence SEQ ID No. 3, respectively the amino acid region (i) identical to the 1-19 peptide region in the native E7 protein of sequence SEQ ID No. 3, and the amino acid region (iii) identical to the 30-98 peptide region in the native E7 protein of sequence SEQ ID No. 3. The central amino acid region (ii) of the mutated E7 protein comprises one or more substitutions of one amino acid, or alternatively, comprises one deletion of at least four amino acids, compared to the corresponding 20-29 peptide region of sequence SEQ ID No. 3.

According to the first variation, the amino acid region (ii) of a mutated E7 protein preferably comprises at least two nucleotide substitutions, and might comprise three, four, five, six, seven, eight, nine or ten amino acid substitutions, compared to the corresponding amino acids of the 20-29 peptide region of sequence SEQ ID No. 3 of the native protein. In the embodiment wherein the amino acid region (ii) of the mutated E7 protein comprises ten amino acid substitutions, the amino acid region (ii) of the mutated E7 protein is completely distinct from the corresponding 20-29 peptide region in native E7 protein of sequence SEQ ID No. 3.

Each substitution of an amino acid, in the 20-29 region of the native E7 protein, in order to obtain a mutated E7 protein according to the invention, is preferably carried out so that the substituted amino acid in mutated E7 protein belongs to a distinct "class" from the amino acid corresponding to the native E7 protein, amongst the respectively aromatic, hydrophobic, polar, basic, acidic amino acid classes, or small amino acids, advantageously as follows:

Thr residue in position 20 replaced by a residue other than Ala, Ser, Met and Gly;
  Asp residue in position 21 replaced by a residue other than Glu;
  Leu residue in position 22 replaced by a residue other than Ile and Val;
  Tyr residue in position 23 replaced by a residue other than Phe and Trp;
  Cys residue in position 24 replaced by any distinct amino acid residue;
  Tyr residue in position 25 replaced by a residue other than Phe and Trp;
  Glu residue in position 26 replaced by a residue other than Asp;
  Gln residue in position 27 replaced by a residue other than Asn;
  Leu residue in position 28 replaced by a residue other than Ile and Val; and
  Asn residue in position 29 replaced by a residue other than Gln.

The set of amino acids is formed with the following amino acids: Ala, Arg, Asn, Asp, Cys, Gln, Glu, Gly, His, Ile, Leu, Lys, Met, Phe, Pro, Ser, Thr, Trp, Tyr and Val, as well as their chemically modified derivatives on one or more chemical groups which do not participate in their binding with another amino acid in the sequence of a mutated E7 protein according to the invention.

A preferred mutated E7 protein family consists in the protein family having their Cys residues in position 24 and Glu in position 26 substituted.

A first particularly preferred mutated E7 protein comprising two substitutions of one nucleotide is E7 protein. (CYS24GLY, GLU26GLN).

A second particularly preferred mutated E7 protein comprising two substitutions of one nucleotide is E7 protein (CYS24SER, GLU26GLN).

According to the second variation, the amino acid region (ii) comprises the deletion of five, six, seven, eight, nine or ten consecutive amino acids, compared to the corresponding 20-29 amino acid sequence of sequence SEQ ID No. 3. When the amino acid region (ii) comprises the deletion of ten amino acids, said region (ii) does not comprise any amino acid and the resulting mutated E7 protein consists, from the N-terminal end to the C-terminal end, in the 1-19 region (i) of sequence SEQ ID No. 3 which is directly linked by a peptide binding with the 30-98 region (iii) of sequence SEQ ID No. 3.

A first preferred mutated E7 protein family according to the above-mentioned second variation is the family of proteins comprising the deletion of six consecutive amino acids in region (ii), compared to the 20-29 amino acid corresponding sequence of sequence SEQ ID No. 3.

A third preferred mutated E7 protein according to the invention consists in the protein the amino acid sequence of which comprises the deletion of the corresponding 21 to 26 amino acids of sequence SEQ ID No. 3 in the native E7 protein. Such a mutated E7 protein, also called E7Δ21-26, has the amino acid sequence SEQ ID No. 1 and is encoded by the nucleic acid of sequence SEQ ID No. 2. The region (ii) of the E7Δ21-26 protein has the deletion of six consecutive amino acids, compared to the 20-29 amino acid corresponding sequence of sequence SEQ ID No. 3.

A second preferred family of mutated E7 proteins according to the above-mentioned second variant is the family of proteins comprising the deletion of five consecutive amino acids in the region (ii), compared to the 20-29 amino acid corresponding sequence of sequence SEQ ID No. 3.

A fourth preferred mutated E7 protein according to the invention consists in the protein having its amino acid sequence comprising the deletion of the corresponding 21-25 amino acids of sequence SEQ ID No. 3 of the native E7 protein. Such a mutated E7 protein is also called E7Δ21-25 in the present disclosure. The region (ii) of the E7Δ21-25 protein has the deletion of five consecutive amino acids, compared to the 20-29 amino acid corresponding sequence of sequence SEQ ID No. 3.

It is shown according to the invention that the expression product of the DNA encoding a HPV-16 mutated E7 protein such as hereinabove defined, when combined with an appropriate immunity adjuvant, is able to generate in a mouse a specific humoral and cellular response, thereby allowing to induce a protective anti-tumor immunity being comparable if not higher than that induced by the native E7 protein.

As used herein, "expression product" of the DNA encoding the mutated E7 protein means the protein(s) resulting from the DNA translation (or of the corresponding RNA messenger) encoding the mutated E7 protein as defined hereinabove, in a host cell.

Moreover, it is shown that the expression product encoding the HPV-16 mutated E7 protein according to the invention has an anti-tumor therapeutic activity equal to or higher than that of the native E7 protein.

In addition, an essential feature of the expression product of the DNA encoding the mutated E7 protein according to the invention consists, on the one hand, in the lack of a direct immunosuppressive activity thereof, and on the other hand, in the induction of an immunosuppression blockage induced by the native E7 protein being secreted by cancerous cells.

An object of the present invention is to provide an immunogenic composition inducing an immune response against the native E7 protein of HPV-16 Papillomavirus, without simultaneously inducing an immunosuppression, comprising, as the active ingredient, a non immunosuppressive mutated E7 protein as defined hereinabove in the present disclosure, if need be, in association with one or more excipients or adjuvants for the physiologically compatible immunity.

The invention is also relative to a vaccine composition without any preventive or curative immunosuppressive property towards a cancer caused by a Papillomavirus infection, characterized in that it comprises, as the active ingredient, a non immunosuppressive mutated E7 protein such as defined hereinabove in the present disclosure, in association with one or more physiologically compatible immunity adjuvants.

The present invention also relates to the use of a non immunosuppressive mutated E7 protein such as hereinabove defined, for preparing an immunogenic composition or a non immunosuppressive vaccine composition and inducing the production of an antibody neutralizing the immunosuppressive activity of the native E7 protein.

As illustrated in the examples, an immunogenic composition or a vaccine composition according to the invention induces a cytotoxic cellular immune response towards cells expressing the native E7 protein, or a peptide derived from the native E7 protein. In particular, it is shown in the examples that an immunogenic composition or a vaccine composition according to the invention induces a cytotoxic cellular immune response towards tumor cells expressing the native E7 protein, or a peptide derived from the native E7 protein.

The reference amino acid sequence of HPV-16 native E7 protein is, for example, the sequence disclosed by Seedorf et al. (1985), the access number of which in Swissprot data base is P03129, and which is reproduced in the present disclosure as sequence SEQ ID No. 3. The nucleic acid encoding the HPV-16 native E7 protein comprises the nucleotidic sequence SEQ ID No. 4.

A mutated E7 protein such as defined in the present disclosure could be prepared by any protein synthesis conventional technique, well known to the man of the art.

For example, a mutated E7 protein could be prepared by means of the recombinant DNA technology, for example, by the overexpression of the nucleic acid encoding the latter, in a recombined bacterial cell system, such as recombined E. coli cells, as disclosed by Kieder et al. (1996) and Tucker et al. (1996).

A mutated E7 protein could be prepared as well by means of a chemical synthesis, either in a homogeneous solution, or in a solid phase. A first illustration of an appropriate chemical synthesis technique is for example that disclosed by Houben Weyl (1974).

Also, a mutated E7 protein could be prepared by a chemical synthesis technique in solution or in a solid phase through successive couplings of the different amino acid residues that are to be incorporated (from the N-terminal end to the C-terminal end in liquid phase, or from the C-terminal end to the N-terminal end in a solid phase, a synthesis technique where the amino acid residue N-terminal ends and the side chains are previously blocked by appropriate protective chemical groups. An illustration of such a technique that could be used for synthesizing a mutated E7 protein is that disclosed by Merrifield (1965a; 1965b).

Nucleic Acids Used According to the Invention

According to the invention, a mutated E7 protein could be produced by translating a nucleic acid encoding said mutated E7 protein, for example, a nucleic acid encoding mutated E7 protein of sequence SEQ ID No. 1.

Preferably, any nucleic acid and any polypeptide according to the invention are under an isolated or purified form.

The term "purified" does not require that the material should be present under an absolute purity form, excluding the presence of any other compounds. It is rather a relative definition. A polynucleotide or a polypeptide is at the purified state when the starting material or the natural material has been purified by at least one order of magnitude, preferably 2 or 3 and preferably 4 or 5 orders of magnitude.

The expressions "nucleic acid", "polynucleotide", "oligonucleotide", as well as "nucleotidic sequence" encompass RNA, DNA, cDNA sequences, as well as RNA/DNA hybrid sequences of at least two nucleotides, indifferently under the single strand form or the duplex form.

The term "nucleotide" means both the natural nucleotides (A, T, G, C) as well as the modified nucleotides comprising at least one modification such as (i) a purine analogue, (ii) a pyrimidine analogue or (iii) a sugar analogue, such modified nucleotides being disclosed for example in Application PCT WO 95/04064.

For the purpose of the present invention, a first nucleotide is considered as being "complementary" of a second polynucleotide when each base of the first nucleotide is coupled with the complementary base of the second polynucleotide having its orientation being reversed. The complementary bases are A and T (or A and U), and C and G.

According to a preferred embodiment, the nucleic acid encoding the mutated E7 protein of sequence SEQ ID No. 1 comprises the nucleotidic sequence SEQ ID No. 2.

A nucleic acid such as hereinabove defined is useful mainly when it is implemented for producing the corresponding expression product.

Therefore, the nucleic acid encoding mutated E7 protein comprises, preferably, a regulating polynucleotide controlling the mutated E7 protein expression in a prokaryotic or an eukaryotic host cell.

The regulating polynucleotide comprises at least one promoter sequence capable to initiate the transcription of the DNA encoding a mutated E7 protein in the selected host cell. Such a regulating polynucleotide could also comprise other nucleotidic sequences favouring the expression of the DNA encoding mutated E7 protein for example, the transcription activating sequences well known to the man of the art.

Preferably, a so-called "inducible" promoter will be selected, i.e. a promoter responsive to the presence of a inducing promoter, said promoter managing the transcription of the DNA placed under its control only in the presence of the inducing compound.

The LacZ promoter is an illustrative example of such an inducible promoter.

According to the invention, any molecular biology, microbiology and recombinant DNA conventional technique, well known to the man of the art, could be used in order to prepare a nucleic acid such as defined hereinbelow. Such techniques are disclosed, for example, by Sambrook et al. (1989), Glover (1985), Gait (1984) and Ausubel et al. (1989).

The nucleic acid comprising a DNA encoding a mutated E7 protein according to the invention, placed under the control of a regulating polynucleotide such as defined hereinabove, is included in an expression cassette.

Expression Cassettes

Such an expression cassette can comprise, in addition to the polynucleotide regulating the DNA encoding mutated E7 protein, untranslated sequences located on side 5' of the opened reading frame, so-called "leader" sequences, capable to increase the translation of the expression product, or so-called "terminator" sequences well known to the man of the art.

Most preferably, an expression cassette such as defined hereinabove further comprises a sequence encoding a signal peptide with a view to the production of a fusion polypeptide between said signal peptide and the mutated E7 protein, for example, between said signal peptide and the E7Δ21-26 protein, in order to favour the secretion of the expression product of the DNA encoding the mutated E7 protein and to find the latter mainly outside the cells, for example in the cell culture supernatant. Preferably, the nucleotidic sequence encoding the signal peptide is located immediately on side 5' of the nucleotidic sequence encoding the mutated E7 protein.

Generally, an expression cassette such as defined hereinunder further comprises a selection marker polynucleotide, for example the his gene, in order to positively select the host cells being transformed by the former.

Recombinant Vectors

The nucleic acid encoding a mutated E7 protein such as defined in the present disclosure, if need be after the insertion into an expression cassette, is preferably introduced into a cloning and/or expression recombinant vector, comprising said nucleic acid or said expression cassette, such as defined hereinabove.

As used herein, the term "vector" means a circular or a linear DNA or RNA molecule being indifferently under the form of a single strand or a double strand.

A recombinant vector is indifferently either a cloning vector or an expression vector.

It might be a vector from bacterial or viral origin.

The preferred bacterial vectors according to the invention are for example the Pbr322 vectors (ATCC37017) or also vectors such as PAA223-3 (Pharmacia, Uppsala, Sweden) and pGEM1 (Promega Biotech, Madison, Wis., USA).

Other examples of other marketed vectors include pQE70, pQE60, pWE9 (Qiagen), psiX174, pBluescript SA, pNH8A, pNH16A, pNH18A, pNH46A, pWLNEO, pSV2CAT, pOG44, pXTI, pSG (Stratagene) vectors.

According to a first embodiment, a recombinant vector such as defined hereinabove is used in order to amplify the nucleic acid or the expression cassette being inserted therein, after a transformation or a transfection of the desired cell host.

According to a second embodiment, it could be an expression vector comprising a nucleic acid or an expression cassette such as defined hereinabove, with a view to the transformation of a host cell selected for producing an expression product of the DNA encoding a mutated E7 protein according to the invention.

A recombinant vector such as defined hereinabove also advantageously comprises initiation and stop sequences with the appropriate transcription.

An expression cassette such as defined hereinabove is a particular embodiment of a recombinant vector according to the invention.

In order to allow for the expression of a nucleic acid encoding a mutated E7 protein according to the invention, a nucleic acid, an expression cassette or a recombinant vector such as defined hereinabove should be introduced into a host cell.

Recombinant Host Cells

In order to implement some production modes of a mutated E7 protein such as defined in the present disclosure, use is advantageously made of a host cell transformed by a nucleic acid, an expression cassette or a recombinant vector such as defined hereinabove.

The transformed host cell is advantageously a bacterial cell, such as an *E. Coli* cell, or also a yeast cell, such as a *Saccharomyces cerevisiae* cell.

Such a transformed host cell is advantageously a eukaryotic cell.

A category of preferred recombinant host cells is the mammalians' cells such as mouse cells, transformed by a nucleic acid, an expression cassette as well as a recombinant vector according to the invention.

Method for Obtaining a Nucleic Acid Encoding E7Δ21-26 Protein

The invention also discloses a method for producing a nucleic acid encoding a mutated E7 protein such as defined in the present disclosure, said method comprising the following steps:

(a) carrying out a directed mutagenesis of the nucleic acid encoding native E7 protein, through amplification of said nucleic acid by means respectively of a first nucleotidic primer and a second nucleotidic primer hybridizing with end 3' of the DNA encoding the native E7 protein; and (b) recovering the amplified DNA.

The first nucleotidic primer comprises, in the sequence thereof, the codon sequence encoding for the mutations that are to be inserted into the starting native E7 protein amino acid sequence.

Thus, if it is contemplated to prepare a mutated E7 protein having its region (ii) comprising one or more substitutions of one amino acid, the sequence of the first primer is such that it contains the appropriate codons encoding for the amino acid(s) which is or are being replaced.

If, according to another alternative, it is contemplated to prepare a mutated E7 protein with its region (ii) comprising the deletion of four, five, six and eight, nine or ten consecutive amino acids, compared to the 20-29 amino acid corresponding sequence of sequence SEQ ID No. 3, then the first primer comprises, in its sequence, a first codon encoding for the amino acid immediately located on the N-terminal side of the peptide fragment to be deleted, said first codon immediately precedes a second codon, said second codon encoding for the amino acid immediately located on the N-terminal side of the peptide fragment to be deleted.

The use of the first primer allows for an amplification final product to be produced, in which the desired codons have been modified, said amplification final product encoding the desired mutated E7 protein.

The second nucleotidic primer used in the amplification step (a) could comprise, in addition to a sequence hybridizing with end 3' of the DNA encoding the native E7 protein, also one or more sites for recognition by the endonucleases.

The nucleic acid encoding mutated E7 protein is inserted into a cloning vector or in an expression vector, at a predetermined insertion site, for example through ligation of said nucleic acid with the nucleic acid of the vector, after having previously opened the host vector, for example through a nucleotidic cutting with the help of a restriction endonuclease, preferably at the level of a cloning polysite.

An object of the invention is to provide a composition comprising the mutated E7 protein, such as defined in the present disclosure, and preferably an immunogenic composition or a vaccine composition comprising said mutated E7 protein.

Compositions Comprising the Non Immunosuppressive Mutated E7 Protein of the Invention An object of the invention is to provide any composition comprising a non immunosuppressive mutated E7 protein according to the invention, such as the mutated E7 protein comprising the amino acid sequence of sequence SEQ ID No. 1.

Another object of the invention is also any composition comprising the expression product of the DNA encoding a mutated E7 protein according to the invention such as the E7Δ21-26 protein of sequence SEQ ID No. 2.

It has been shown according to the invention that a mutated E7 protein such as defined in the present disclosure lacks any immunosuppressive property, as is illustrated in the examples.

In particular, it has been shown that the E7Δ21-26 protein did not induce any immunosuppression when it is administered to a mammalian, in association with an appropriate immunity adjuvant.

It has also been shown that the mutated E7 proteins, respectively the E7 protein (CYS24GLY, GLU26GLN) and the E7 protein (CYS24SER, GLU26GLN) did not induce any immunosuppression when administered to a mammalian, in association with an appropriate immunity adjuvant.

As this has already been briefly explained previously, the expression product of the DNA encoding the mutated E7 protein of sequence SEQ ID No. 1 induces an immune response towards the native E7 protein at least of the same order as the immune response induced by the native E7 protein itself, and the mutated E7 protein according to the invention lacks, on human immune cells, the immunosuppressive properties that characterize more particularly the native E7 protein.

Another object of the invention is therefore a preventive or curative pharmaceutical composition of a HPV-16 infection, and more specifically of a cancer induced by PHV-16, characterized in that it comprises, as the main active ingredient, the expression product of the DNA encoding the mutated E7 protein such as defined hereinabove, if need be, in association with one or more physiologically compatible excipients.

Preferably, said pharmaceutical composition is present in a form adapted to the administration of a weekly amount ranging from 10 to 1000 μg of the mutated E7 protein, or the expression product of the DNA encoding the latter.

It is shown according to the invention that the expression product of the DNA encoding the mutated E7 protein of sequence SEQ ID No. 1, when being administered in combination with an appropriate immunity adjuvant, is capable to generate a humoral and cellular immune response directed towards the native E7 protein, thereby allowing to induce a preventive immunity towards tumors. In addition, the protective immunity inducing an anti-tumor resistance condition caused by the administration of the expression product of the DNA encoding the mutated E7 protein is equal to or higher than that obtained after previous immunization with the native E7 protein.

It has also been shown that the expression product of the DNA encoding the mutated E7 protein of sequence SEQ ID No. 1 is capable to induce a therapeutic anti-tumor immunity, when such a protein is administered, in association with an appropriate immunity adjuvant, to an individual having already developed tumors. The therapeutic anti-tumor immune response induced by the expression product of the DNA encoding the mutated E7 protein is significantly higher than that which could be obtained after administering the native E7 protein.

Such results are illustrated in example 3 where it is shown, in a murine model, that the anti-tumor therapeutic immunity induced by the expression product of the DNA encoding the mutated E7 protein allows to extend the animals' mean life time by 1.5 times, as compared to the mean life time of animals being administered the native E7 protein.

It has also been shown that the preventive anti-tumor immunity of the therapeutic anti-tumor immunity induced by the expression product of the DNA encoding the mutated E7 protein was due to the simultaneous induction of a specific humoral and cellular immune response.

Thus, the results of the examples show that a mutated E7 protein such as defined in the present disclosure is able to induce a systemic humoral response towards the native E7 protein. It has more particularly been shown that a high level of IgG isotype anti-E7 antibody was produced, mainly of the IgG2b and IgG1 isotype antibodies.

Additionally, administering a mutated E7 protein according to the invention to an individual, under the appropriate conditions, also makes it possible to induce a mucosal type immunity, as evidenced by the high level of IgA isotype antibody response presented in example 3.

In addition, according to an essential feature of the mutated E7 protein, such a protein which itself lacks any direct immunosuppressive activity of the native E7 protein, also allows to block the immunosuppressive activity of the soluble E7 protein secreted by cancerous cells, by virtue of the neutralizing character of the antibodies produced after immunization with the mutated E7 protein, as evidenced by the results in example 2.

The results of the examples also show that a mutated E7 protein according to the invention allows for the proliferation of CD4+ and CD8+ T-cells specifically recognizing the native E7 protein, such a cellular proliferation being accompanied with an overproduction of the γ-IFN cytokine.

The invention is also relative to an immunogenic composition inducing an immune response towards the HPV-16 Papillomavirus native E7 protein, without simultaneously inducing an immunosuppression, said composition comprising, as the active ingredient, a non immunosuppressive mutated E7 protein, with the amino acid sequence consisting, from the N-terminal end to the C-terminal end, in:
  i. the 1-19 amino acid sequence of sequence SEQ ID No. 3;
  ii. an amino acid sequence possessing (a) the substitution of at least one amino acid, compared to the 20-29 corresponding amino acid sequence of sequence SEQ ID No. 3 or (b) the deletion of at least four consecutive amino acids, compared to the 20-29 corresponding amino acid sequence of sequence SEQ ID No. 3; and
  iii. the 30-98 amino acid sequence of sequence SEQ ID No. 3, in association with one or more physiologically compatible immunity excipients or adjuvants.

Such an immunogenic composition could be used preventively, with the aim to induce a protective anti-tumor immunity towards a HPV-16 infection.

Such an immunogenic composition could also be used therapeutically or curatively, for a HPV-16 infection, in particular of a cancer caused by a HPV-16 infection.

The invention also relates to the use of a mutated E7 protein such as defined in the present disclosure for preparing a pharmaceutical composition, or for preparing an immunogenic composition such as described hereinabove.

Another object of the present invention is also a method for preparing a pharmaceutical composition, or an immunogenic composition, intended for inducing a preventive protective immunity or a therapeutic immunity against a cancer caused by a HPV-16 infection, while blocking the immunosuppression condition induced by the native E7 protein, characterized in that it comprises a step wherein a mutated E7 protein such as defined hereinabove is combined with one or more physiologically compatible immunity adjuvants.

The invention is also relative to a preventive or curative vaccine composition for a cancer caused by a Papillomavirus infection, characterized in that it comprises, as the active ingredient, a non immunosuppressive mutated E7 protein, with the amino acid sequence consisting, from the N-terminal end to the C-terminal end, in:
  i. the 1-19 amino acid sequence of sequence SEQ ID No. 3;
  ii. an amino acid sequence possessing (a) the substitution of at least one amino acid, compared to the 20-29 corresponding amino acid sequence of sequence SEQ ID No. 3 or (b) the deletion of at least four consecutive amino acids, compared to the 20-29 corresponding amino acid sequence of sequence SEQ ID No. 3; and
  iii. the 30-98 amino acid sequence of sequence SEQ ID No. 3, in association with one or more physiologically compatible immunity adjuvants.

In order to fight against the local immunosuppression at the level of the HPV-16 infected cancerous cells, being induced by the extracellular E7 protein, and then to stimulate an efficient immune response towards such cancerous cells, having at their membrane surface the native E7 protein, or peptides derived from the native E7 protein after an intracellular maturation, in association with a MHC class I antigen, it is important to induce the antibody production, more specially of IgG isotype antibodies, capable to neutralize the immunosuppressive effect of the soluble E7 protein secreted by cancerous cells infected by the HPV-16 virus. Moreover, it is essential to simultaneously induce the protection of cytotoxic lymphocytes (CTL) able to specifically recognize the native E7 protein, or a peptide being derived therefrom, exposed at the membrane surface of cancerous cells, in order to destroy such cells. In order to achieve those objectives, it is necessary to induce a systemic type immune response.

In addition, the human Papillomaviruses being detected mainly in mucous membrane cancers, in particular in anogenital cancers, including the uterine neck cancer in woman, it is important to supplement the preventive or therapeutic effects of the induction of a systemic type immune response by the induction of a mucosal type immune response, more particularly in stimulating the production of IgA isotype antibody production at the local level, on the mucous membranes.

Depending on the objectives to be reached, immunity adjuvants are used, capable to orient the response towards a systemic or mucosal immunity.

Amongst the systemic immunity adjuvants, IFA type adjuvants (incomplete Freund's adjuvant), calcium phosphate or alumina hydroxide are preferably used. The QuilA adjuvant marketed by Brenntay Biosector, Denmark, can be also used. Amongst the mucosal immunity adjuvants, are preferably used adjuvants such as choleratoxin B (CTB) as well as a LT toxin mutant (LTμ), well known to the man of the art.

Inducing a systemic type and/or a mucosal type immune response is also influenced by the administration route of the vaccine composition of the invention.

Thus, administering the vaccine composition through parenteral, subcutaneous or intradermal route will favor the induction of a systemic immune route, accompanied, if need be, also with a mucosal immune response.

Thus, administering the vaccine composition according to the invention at the local level, for example through nasal instillation, or also through local application at the surface of the mucous membranes, will favor the induction of a mucosal type immune response.

Another object of the present invention is also a method for a preventive or curative treatment of a cancer caused by a HPV-16 infection, characterized in that it comprises a step wherein the patients are administered an immunologically efficient amount of a vaccine composition such as defined in the present specification.

Preferably, the patient is administered, under a form adapted to the systemic and/or mucosal administration, a vaccine composition of the invention, in a sufficient amount for being preventively or therapeutically efficient, for a subject in need of such a treatment. The administered dose of the mutated E7 protein or the expression product of the DNA encoding the mutated E7 protein, could range for example from 10 to 1000 µg through parenteral route, once a week for 2 months, then periodically depending on the level of the induced cellular or humoral response, for example every two to six months.

According to a first aspect, the vaccine composition according to the invention is characterized in that it comprises at least one adjuvant able to preferentially orient the immune response towards the production of antibodies neutralizing the immunosuppressive activity of the wild E7 protein.

According to a first particular embodiment, said vaccine composition is characterized in that it comprises at least one adjuvant able to preferentially orient the immune response towards the production of IgA isotype antibodies.

According to a second preferred embodiment, said vaccine composition is characterized in that it comprises at least one adjuvant able to preferentially orient the immune response towards the production of IgG isotype antibodies.

According to still another preferred embodiment, a vaccine composition according to the invention is characterized in that it comprises the combination (i) of an adjuvant able to preferentially orient the immune response towards the production of an IgA isotype antibody and (ii) of an adjuvant able to preferentially orient the immune response towards the IgG isotype antibody production.

Preferably, the vaccine composition according to the invention is characterized in that it comprises at least one immunity adjuvant able to induce both humoral and cellular immune response.

Preferably, the induction of a cellular response will be looked for, characterized in particular by the proliferation of T lymphocytes expressing the CD8 antigen and specifically recognizing the wild E7 protein, such as shown at the surface of cancerous cells in association with the HMC class I antigens.

According to another particular embodiment of a vaccine composition according to the invention, such a vaccine composition could comprise one or more other antigenic or immunogenic compounds of HPV. For example, in a vaccine composition according to the invention, the expression product of the DNA encoding the mutated E7 protein could be associated to one or more HPV-16 capsid proteins or to peptides obtained from such capsid proteins, in particular L1 and L2 proteins of HPV-16 well known to the man of the art.

According to still another particular embodiment, the vaccine composition according to the invention could comprise one or more antigenic or immunogenic compounds able to induce a cellular or humoral immune response towards HPV types distinct from the HPV-16, preferably towards HPV types in order to cause cancers, such as HPV-18, 31, 33 and 51.

In still another particular embodiment of a vaccine preparation according to the invention, the expression product of the DNA encoding the mutated E7 protein could be combined with one or more antigenic or immunogenic compounds able to induce the production of antibodies towards soluble factors with immunosuppressive or angiogenic properties such as αIFN, βTGF, αTNF or even VEGF. Preferably such antigenic or immunogenic compounds are respectively the chemically modified αIFN, βTGF, the αTNF or VEGF so as to induce their immunosuppressive properties and/or to stabilize them. Such chemical modifications, for example, through carboxymethylation, are well known to the man of the art. These are more particularly described by Frankel et al. (1988).

According to a preferred aspect of such a particular embodiment of a vaccine composition according to the invention, the expression product of the DNA encoding the mutated E7 protein and at least one antigenic or immunogenic compound are chemically linked to form a super immunogenic compound such as disclosed in French patent application No. 01/10751 filed on $10^{th}$ Aug. 2001 in the name of NEOVACS Corporation.

Composite Superimmunogens

Such a composite superimmunogen comprises two distinct immunogenic polypeptides, physically linked one to the other, both polypeptides respectively consisting in:
  (a) a first immunogenic polypeptide inducing a cellular immune reaction, or a cellular and humoral immune reaction, against a HPV-16 cellular pathogenic antigenic structure;
  (b) a second immunogenic polypeptide inducing the production of neutralizing or blocking antibodies against a local circulating protein of the stroma selected amongst a cytokine factor or a cell regulating factor with immunotoxic or angiogenic properties, such a factor being produced by cancerous cells, or by stroma cells, including T lymphocytes and cells having the antigen (APC).

The composite superimmunogen used according to the invention is called "bifunctional" as both polypeptides (a) and (b, which are the two essential parts building it up, allow for the simultaneous induction of an immune reaction directed against two distinct targets, respectively the pathogenic antigenic structure and the local circulating protein of the stroma. However, a bifunctional composite superimmunogen according to the invention could comprise in the structure thereof a plurality of copies respectively of a polypeptide (a) and/or a polypeptide (b).

The polypeptide (a) and the polypeptide (b) building up a composite superimmunogenic compound of the invention are so-called "physically linked" one to another as they are in all cases both included in the same physical structure, molecule or particle (microparticle or nanoparticle) within which they are somewhat apart from one another. As they are physically linked to one another in the composite superimmunogen, the polypeptide (a) and the polypeptide (b) are presented together to the same immunocompetent cells as well as the macrophages as the T or B lymphocytes.

According to a first preferred embodiment of a composite superimmunogen, the polypeptides (a) and (b) are respectively selected amongst:
  Polypeptide (a): L1 and L2 proteins of the HPV-16 Papillomavirus, detoxicated or stabilized if needed, of the immunogenic fragments of such proteins, or also an immunogenic protein being derived therefrom (Le Buanec et al., 1999);

Polypeptide (b): a mutated E7 protein according to the invention, for example, a mutated E7 protein of sequence SEQ ID No. 1.

According to a second preferred embodiment of a composite superimmunogen, the polypeptides (a) and (b) are respectively selected amongst:

Polypeptide (a): a mutated E7 protein according to the invention, for example, the mutated E7 protein of sequence SEQ ID No. 1

Polypeptide (b): the IFNα, TGFβ, TNFα and VEGF proteins, detoxicated or stabilized if needed, of the immunogenic fragments of such proteins, or an immunogenic protein being derived therefrom.

According to an advantageous embodiment, the invention also relates to a composition comprising several composite superimmunogens being distinguished by the identity of the mutated E7 protein (polypeptide (a) or polypeptide (b), depending on the type of composite superimmunogen).

In order to prepare a composite superimmunogen according to the invention, a coupling is made of the polypeptide (a) and the polypeptide (b) through a chemical route or through a genetic recombination.

In a particular embodiment of the immunogenic peptidic conjugate of the invention, the polypeptides (a) and (b) are directly linked between one another covalently, for example, by means of a peptide-CO—NH link.

However, in order to introduce some flexibility in the structure of the immunogenic peptidic conjugate, and more particularly in order to allow for some mobility in the space of the polypeptides (a) and (b), relative to one another within the immunogenic peptidic conjugate, a peptide conjugate is preferred within which the polypeptides (a) and (b) are separated from one another, within said conjugate, by a spacer chain.

According to a first preferred embodiment of an immunogenic peptidic conjugate, the polypeptides (a) and (b) are separated from one another, within said conjugate, by a spacer chain selected amongst SMCC or SIAB, being both bifunctional compounds.

The SIAB compound, described by Hermanson G. T. (1996, Bioconjugate techniques, San Diego: Academic Press, pp 239-242), is the compound with the following formula (I):

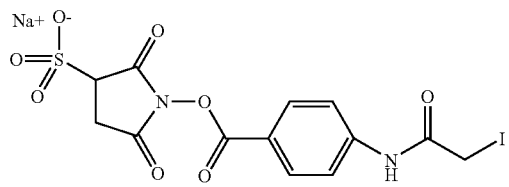

The SIAB compound comprises two reactive groups, respectively an iodoacetate group and a Sulfo-NHS ester group, those groups reacting respectively on amino and sulfhydryl groups.

The SMCC compound, being described by Samoszuk M. K. et al. (1989, Antibody, Immunoconjugates Radiopharm., 2(1): 37-46), is the compound with the following formula (II):

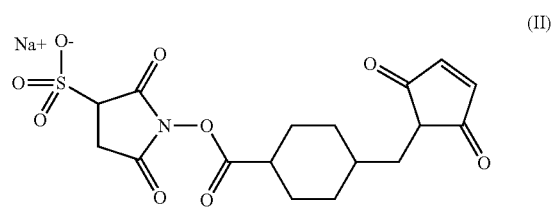

The SMCC compound comprises two reactive groups, respectively a Sulfo-NHS ester group and a maleimide group, reacting respectively with an amino group and a sulfhydryl group.

According to a second preferred embodiment, the composite superimmunogen comprising a spacer chain comprising a linear spacer peptide. Preferably, a linear spacer peptide will be selected, being 3 to 30 amino acid long, advantageously 5 to 20 amino acid long and most preferably, 7 to 15 amino acid long.

Preferably, the linear spacer peptide is essentially, even exclusively, made up of positively or negatively charged amino acids, with a pH equal to 7.0 in order to increase the overall hydrophilicity of said composite superimmunogen. It will be understood that it should be avoided to use spacer peptides comprising hydrophobic amino acids. Preferably, the spacing peptide is characterized in that it is made up of a poly(lysine) chain being 3 to 30 lysine residue, advantageously 5 to 20, and most preferably, 7 to 15 lysine residue long.

According to still another embodiment of a composite superimmunogen according to the invention, the polypeptides (a) and (b) are separated from one another, within said peptidic conjugate, by a spacer chain consisted of one branched spacer peptide, preferably a poly(lysine) oligodendrimeric structure, such as described for example by Basak et al. (1995).

In the latter embodiment of a composite superimmunogen according to the invention, said peptidic conjugate might comprise several copies of polypeptides (a) and (b) per conjugate molecule, advantageously 2 to 8 copies of polypeptides (a) and (b), and preferably, no more than 4 copies of each of the polypeptides (a) and (b) per conjugate molecule.

The polypeptides (a) and (b) could also be included both in one single physical structure for example on nanoparticles with a diameter ranging from 10 to 500 nanometres, preferably from 10 to 2000 nanometres, and most preferably from 10 to 100 nanometres, for example, nanoparticles of IMS, as described by Aucouturier et al. (2001), of chitosan, as described for example by Skaugrud et al. (1999), of liposomes or biodegradable particles such as acidic polylactide (PLA), poly-ε-caprolactone (PLC) or poly(lactide-coglycolide) (PLG) described by Baras et al. (1999).

According to still another embodiment, the polypeptides (a) and (b) are physically linked within one single carrier structure allowing for their simultaneous presentation to the cells of the immune system. In such a particular embodiment, the polypeptides (a) and (b) are immobilized on nanoparticles, for example chitosan, IMS (Immunomodulator available from the Seppic Corporation, France) consisted of lipidic nanoparticles with a diameter ranging from 100 to 300 nanometres) or liposomes.

Preferably, such nanoparticles have a small size so as to simultaneously present the polypeptides (a) and (b) to the cells, as if such polypeptides were linked covalently within the same molecule. Advantageously, the nanoparticles have a diameter ranging from 10 to 1000 nm, preferably from 10 to 500 nm, more preferably from 10 to 300 nm and most preferably from 10 to 200 nm.

Vaccine Compositions Containing a Nucleic Acid Encoding the Mutated E7 Protein According to the Invention Another object of the invention is to provide an immunogenic composition, or a vaccine composition without any preventive or curative immunosuppressive property, for a cancer caused by a Papillomavirus infection, characterized in that it comprises an immunologically efficient amount of a nucleic acid encoding a mutated E7 protein, such as defined in the present disclosure, an expression cassette or also a recombinant vector such as defined in the present disclosure.

For implementing the above-mentioned vaccine composition, a retroviral vector or also an adeno-associated vector (AAV) is preferred as the expression vector. Such adeno-associated vectors are for example described by Flotte et al. (1992), Samulski et al. (1989), or also by McLaughlin et al. (1996). In order to introduce nucleic acids, expression cassettes or vectors into a host cell, the man of the art could advantageously make use of various techniques, such as the calcium phosphate precipitation technique (Graham et al), 1973, Chen et al. 1987), dextran DEAE (Gopal, 1985), the electroporation (Turkaspa, 1986, Potter et al. 1984), the direct micro-injection (Harland et al., 1985) or also DNA loaded liposomes (Nicolau et al., 1987; Fraley et al., 1980).

According to a particular embodiment, a method for introducing a nucleic acid or an expression cassette according to the invention into a host cell, in particular a host cell originating from a mammalian, in vivo, comprises a step wherein a preparation is introduced comprising the nucleic acid or the expression cassette in a pharmaceutically compatible carrier, through local injection at the level of the selected tissue, for example a smooth muscle tissue or a mucosal tissue, the nucleic acid and the expression cassette being absorbed by the cells of such a tissue.

Compositions for the in vitro and the in vivo use comprising "bared" nucleic acids or expression cassettes are, for example, disclosed in PCT application no WO 95/11307 as well as in the articles by Tacson et al. (1996) and Huygen et al. (1996).

It could also be adenoviral vectors such as type 2 or 5 human adenovirus.

The vector amount to be injected in the selected host organism varies depending on the injection site. By way of an indication, between about 10 µg and 1000 µg could be injected of the nucleic acid or the expression cassette encoding the mutated E7 protein according to the invention in a patient body.

Compositions Adapted for the Anti-tumor Passive Vaccination

As is clearly illustrated in the present disclosure, the systemic or mucosal antibody production is essential in order to block the immunosuppressive properties of the E7 protein secreted by the HPV-16 infected cancerous cells.

In the situation where a vaccine composition comprising a mutated E7 protein according to the invention or the vaccine composition comprising a nucleic acid, an expression cassette or a recombinant vector encoding the mutated E7 protein, is used therapeutically, i.e. after the HPV-16 infection event, it is advantageous to quickly block the immunosuppressive effect of the E7 protein produced and secreted by cancerous cells in order to favour the quick induction of a humoral and cellular immune response by said vaccine composition, with a view to further increasing the efficiency thereof.

The early blocking of the immunosuppressive effect of the E7 protein produced by infected cells could be done administering patients an efficient amount of neutralizing antibodies obtained after immunization of man or animal towards the native E7 protein, using a mutated E7 protein of the invention as the antigenic or immunogenic compound, in association with one or more appropriate immunity adjuvants.

The invention also relates to a method for separating antibodies neutralizing the immunosuppressive effect of the HPV-16 native E7 protein, characterized in that it comprises a step wherein a mammal is immunized, including man, using a mutated E7 protein of the invention, followed by the recovery of the resulting antibodies.

The invention is also relative to antibodies directed against a mutated E7 protein of the invention. Such antibodies are more particularly characterized in that they are neutralizing, i.e. they neutralize the immunosuppressive effect of the native E7 protein.

The invention has also as an object a pharmaceutical composition containing antibodies neutralizing the immunosuppressive effect of the HPV-16 native E7 protein, in particular the E7 protein secreted by HPV-16 infected cells, said antibodies being directed against a mutated E7 protein according to the invention.

It also relates to a composition for the passive vaccination directed against a HPV-16 infection, including against a cancer caused by a HPV-16 infection, containing the antibodies as defined hereinabove.

In order to check the neutralizing ability of the antibodies according to the invention, the man of the art could advantageously refer to the test described in example 1, consisting in quantifying the inhibition percentage of the α-IFN or α-TNF production by human macrophages exposed to the native E7 protein.

Another object of the invention is a method for blocking the immunosuppressive effect of the E7 protein produced by HPV-16 virus infected cells, characterized in that the patients are administered a neutralizing amount of antibodies obtained after the immunization of man or the animal with a mutated E7 protein such as defined in the present disclosure.

The "neutralizing amount" of antibodies to be administered to the patient varies depending on the HPV infection extent. In general, the patient is administered an amount of neutralizing antibodies corresponding to the amount of neutralizing antibodies required to block the immunosuppressive amount of a native E7 protein ranging from 100 ng to 1 mg, in the immunosuppression test described in example 1.

The antibodies can be IgA isotype or IgG isotype antibodies. They can be polyclonal antibodies or also monoclonal antibodies.

The antibodies according to the invention also encompass F(ab')$_2$ or F(ab) fragments.

Vaccine Composition Comprising Dendritic Cells Treated with a Mutated E7 Protein According to the Invention Dendritic cells are antigen presenting cells (APC) being specialized in the initiation of the T cellular immunity. A physical contact between dendritic cells and T cells is required for the induction of an immune response of T cells. Dendritic cells activate the specific immune response of a given antigen, through two signalisation steps. The first signalisation step involves an antigenic peptide-MHC/T cell receptor (TCR) interaction. The second signalisation step involves co-stimulating molecules such as cellular surface markers and cytokines.

Dendritic cells produce various cytokines when they present the antigen to the T cells, influencing the cytokine micro-environment, then the subsequent immune response.

More specifically, it is known that the vaccination with dendritic cells allows to break the immune tolerance of the immune system towards tumoral cells and induces the lysis of the tumor in the host organism through the stimulation of a T cellular immune response of Th1 type, at least in the cancers for which there is no concomitant immunosuppression situation existing with the tumor development.

It has been shown according to the invention that the in vitro incubation of a dendritic cell population of an individual with an appropriate amount of a mutated E7 protein, such as defined in the present disclosure, makes the dendritic cells able to subsequently present said mutated E7 protein to the T cells present in a population of autologous mononucleated cells, obtained from the same individual, and to induce the activation of the specific T cells of the E7 protein, which is visualized by the proliferation of such T cells. The activation of T cells could be measured, for example, by the amount of intracellular incorporation of [$^3$H] thymidine, as illustrated in the example.

In a similar experiment, but wherein the dendritic cells are previously in vitro incubated with the native E7 protein, no activation of T cells is observed, as in the population of control dendritic cells incubated in the absence of any exogenous antigen. In such a system, once more, the immunosuppressive activity of the native E7 protein can be observed.

On the contrary, a mutated E7 protein according to the invention lacks any immunosuppressive activity and allows for the induction of an efficient specific T cellular immune response against the native E7 protein.

The invention also has the object to provide a vaccine composition lacking any preventive or curative immunosuppressive property towards a cancer caused by a Papillomavirus infection, characterized in that it comprises, as the active ingredient, an appropriate amount of autologous or allogenic dendritic cells towards the individual to be treated, said autologous dendritic cells having been incubated with a mutated E7 protein such as defined in the present invention and thereby made able to present said mutated E7 protein to the T cells, specifically recognizing it.

Another object of the invention is also a method for preventing or curing a cancer caused by a Papillomavirus infection, characterized in that it comprises a step wherein an individual to be treated is administered an appropriate amount of autologous (isogenic) dendritic or allogenic cells towards the individual to be treated, said autologous (isogenic) or allogenic dendritic cells having been incubated, prior to their administration to the individual, with a mutated E7 protein such as defined in the present disclosure and thereby made able to present said mutated E7 protein to the T cells, specifically recognizing it.

Preferably, dendritic cells are obtained through differentiation of monocytes prepared by elutriation from human peripheral blood, either the patient's blood or blood from an individual sharing with the patient a haplotype of the histocompatibility major complex, such as a HLA-A2 haplotype.

Preferably, dendritic cells, once taken from the patient, are cultured in an appropriate culture medium for the culture of mammal's cells such as the HL1 medium (Bio Whittaker), if need be added with glutamine, and optionally also with one or more antibiotics, such as streptomycine and the culture is done at 37° C. in an incubator in a wet atmosphere and at 5% (V/V) $CO_2$.

The dendritic cells in culture are then incubated with a selected amount of the mutated E7 protein, preferably an amount ranging from 5 to 50 µg/ml.

Preferably, the dendritic cells are incubated with the mutated E7 protein, with a mutated E7 protein amount per $10^6$ dendritic cells ranging from 1 to 50 µg.

Preferably, the patient to be treated is administered an amount of dendritic cells treated with a mutated E7 protein according to the invention ranging from $10^1$ to $500 \times 10^6$ cells.

Advantageously, a single administration is applied to the patient, through injection via the parenteral route, of the dendritic cells treated by the mutated E7 protein. If needed, multiple injections can be administered to the patient depending on the intensity of the anti-E7 immune response being caused, for example, a monthly, bimonthly, quarterly or biannual administration of the treated dendritic cells.

The invention is further illustrated, with no limitation, by the following figures and examples.

FIG. 16 illustrates graphs showing the development of C3 tumors in mice having received $7 \times 10^3$ C3 cells expressing HPV-16 E7; FIG. 16A represents control mice, whereas

Figure 18:
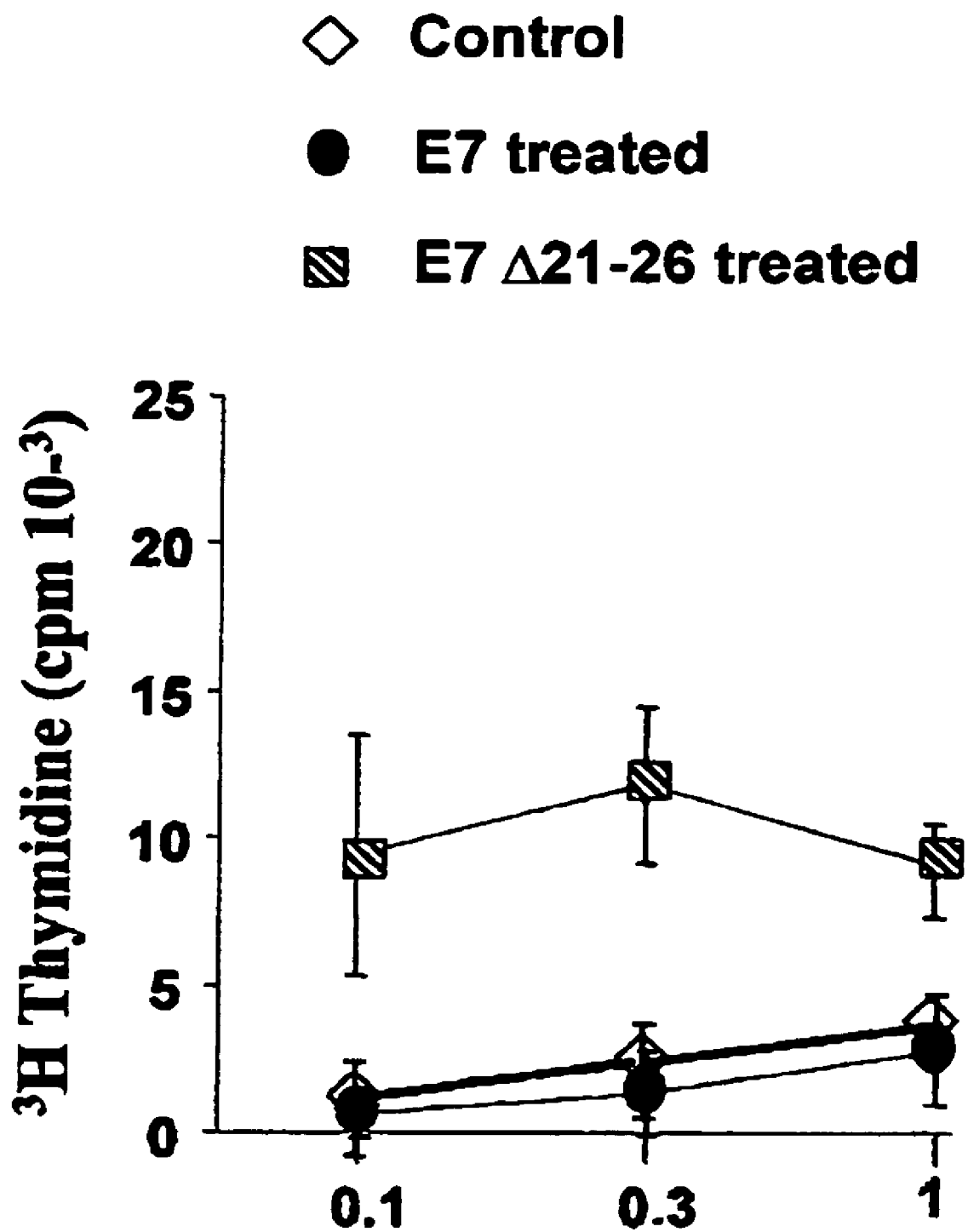

FIG. 17 illustrates graphs showing the development of C3 tumors in mice having received "$9 \times 10^3$" C3 cells expressing HPV-16 E7; and FIG. 18 is a graph showing the mixed lymphocyte reaction level, measured by the proliferation level of effector mononucleated cells stimulated by control dendritic cells (empty lozenge), pretreated with the native E7 protein (full circle) or pretreated with the E7Δ21-26 protein (hatched square). The ordinates give the proliferation of effector mononucleated cells visualized by the incorporation of [3H] thymidine, whereas the abscissas gives the ratio between the stimulating cell number (dendritic cells) and the effector cell number (T cells).

EXAMPLE 1

Systemic (Humoral and Cellular) Immune Response

Example 1.1

Immunogenic Activity of the E7Δ21-26 Protein in the Presence of a FREUND's Complete (ACF) and Incomplete (AIF) Adjuvant The immunogenic (humoral and cellular) activity of the E7Δ21-26 preparation has been studied in 6 week old C57BL/6 (H-$2^b$) female mice, purchased from Charles River, in the presence of ACF and AIF.

A. Material and Methods

At day 0, a group of 6 mice receives a 0.2 ml (50 μg) injection of an ACF emulsion through intramuscular route. An AIF 5 μg booster injection is given at day 21 and day 60.

A blood sample is taken at the retro-orbital level from each mouse before the first injection at day −2 and 12 days after the last immunization.

8 control mice receive the same immunogen-free preparations.

3 mice receive 100 μg of the preparation and the absence of disease symptoms is studied during the 7 days following the injection.

The mice are challenged with C3 cells, 12 days after the last immunization. C3 cells are embryo cells from C57BL/6 origin, transformed with the full HPV16 genome and the ras oncogene (Feltkamp, M. C., H. L. Smits, M. P. Vierboom, R. P. Minnaar, B. M. de Jongh, J. W. Drijhout, J. ter Schegget, C. J. Melief, and W. M. Kast. 1993. Vaccination with cytotoxic T lymphocyte epitope-containing peptide protects against a tumor induced by human Papillomavirus type 16 transformed cells. Eur. J. Immunol. 23:2242-2249). They are cultured in DMEM medium (Bio-Whittaker) added with 10% FCS, 50 U/ml penicillin, 50 μg/ml streptomycin and 250 ng/ml fongizone at 37° C. in a humid atmosphere containing 7% $CO_2$. The cells that are to be injected to the mice are washed in serum free medium after being removed from the plastic using trypsin.

The lack of toxicity in the preparation is measured by the absence of clinical signs: (behaviour, hairs, weight) and through anatomic study after necropsy.

B. Results

The mice immunized by means of the E7 Δ21-26 preparation, in the presence of ACF and AIF, do not show any clinical sign and no anatomic injury.

No one of the three mice immunized with 100 μg of the preparation shows any disease symptoms during the 7 days following the injection.

The immune response is measured by:
1. Humoral Response

The presence in the serum of IgG type antibodies directed against the native E7 recombinant protein is measured by ELISA and expressed in titer (reverse of the dilution giving an optical density higher than 0.3).

FIG. 1

The mice immunized with the E7 Δ21-26 preparation, in the presence of ACF and AIF, have very high anti-E7 IgG type antibody titers.

The neutralizing activity of such antibodies is measured using the following immunosuppression test. A 1/50 dilution of the serum taken at day −2 and day 72 is incubated for 2 hours with 50 ng/ml of native E7. These dilutions are then applied on human macrophages, pretreated with γ-IFN for 16 hours. After 24 hours of culture, the culture supernatants are recovered and the produced α-TNF amount is measured by an ELISA test, the DTA50 DuoSet (R&D). The neutralizing serums prevent the E7 protein from inducing the expression of α-TNF, while the non neutralizing serums allow for the synthesis of this cytokine.

The results are given in neutralization %.

FIG. 2

The antibodies induced by the E7 Δ21-26 preparation in the presence of ACF followed with AIF have a very high neutralizing power.

2. Cellular Response
   2.1. Cellular Proliferation

Spleen cells from immunized mice and control mice are isolated and then cultured in round bottom wells of a microculture plate at 100,000 cells/well in the presence of native E7. The cellular culture is continued at 37° C. in a wet atmosphere loaded with 5% $CO_2$ for 6 hours. 18 hours before the end of the incubation, 0.5 μCi of tritiated thymidine/well is added. The immune response intensity of is proportional to the Ip proliferation index.

$Ip=spm$ (strokes per minute) for the given antigen/ control $spm$

FIG. 3

Spleen cells from mice immunized with the E7 Δ21-26 preparation, in the presence of ACF and AIF, proliferate when they are activated in vitro with the native E7 protein.

2.2. Production of γ-IFN

The presence of gamma IFN in the culture supernatants of the spleen cells cultured in the presence of 10 μg/ml of native E7 is determined, after 72 hours of culture, using an ELISA test (LO-IMEX, Belgium) as previously described (De Smedt, T., B. Pajak, E. Muraille, L. Lespagnard, E. Heinen, P. De Baetselier, J. Urbain, O. Leo and M. Moser. 1996. Regulation of dendritic cell numbers and maturation by lipopolysaccharide in vivo. J. Ex. Med. 184:1413-1424). The results are expressed in IU/ml.

FIG. 4

The spleen cells of mice immunized with the E7 Δ21-26 preparation in the presence of ACF followed by AIF produce a high amount of gamma IFN when they are activated in vitro with the native E7 protein.

Example 1.2

Immunogenic Activity of the E7Δ21-26 Protein in the Presence of a FREUND's Incomplete Adjuvant (AIF)

The immunogenic (humoral) activity of the E7Δ21-26 preparation has been studied in 6 week old C57BL/6 (H-2$^b$) female mice purchased from Charles River, in the presence of AIF.

A. Material and Methods

At day 0, a group of 6 mice receives a 0.2 ml (50 μg) injection of an AIF emulsion in the presence of 1 μg murine GM-CSF and 1.5 μg murine IL-2 through intramuscular route. An AIF 5 μg booster injection is given at day 21 and day 60.

A blood sample is taken at the retro-orbital level from each mouse before the first injection at day −2 and 12 days after the last immunization.

- 6 control mice receive the same immunogen-free preparations.
- 3 mice receive 100 μg of the preparation and the absence of disease symptoms is studied during the 7 days following the injection.

The lack of toxicity in the preparation is measured by the absence of clinical signs: (behaviour, hairs, weight) and through anatomic study after necropsy.

B. Results

The mice immunized by the E7 Δ21-26 preparation in the presence of AIF do not show any clinical sign and no anatomic injury.

None of the three mice immunized with 100 μg of the preparation shows any disease symptoms during the 7 days following the injection.

The immune response is measured by:

1. Humoral Response

The presence in the serum of IgG type antibodies directed against the native E7 recombinant protein, is measured by ELISA and expressed in titer (reverse of the dilution giving an optical density higher than 0.3).

FIG. 5

The mice immunized with the E7 Δ21-26 preparation in the presence of AIF have very high anti-E7 IgG type antibody titers.

The neutralizing activity of such antibodies is measured using the following immunosuppression test. A 1/50 dilution of the serum taken at day −2 and day 72 is incubated for 2 hours with 50 ng/ml of native E7. These dilutions are then applied on human macrophages, pretreated with γ-IFN for 16 hours. After 24 hours of culture, the culture supernatants are recovered and the produced α-TNF amount is measured by an ELISA test, the DTA50 DuoSet (R&D). The neutralizing serums prevent the E7 protein from inducing the expression of α-TNF, while the non neutralizing serums allow for the synthesis of this cytokine.

The results are given in neutralization %.

FIG. 6

The antibodies induced by the E7 Δ21-26 preparation in the presence of AIF have a very high neutralizing power.

Example 1.3

Immunogenic Activity of the E7Δ21-26 Protein Embedded in Chitosan Nanoparticles in the Presence of a FREUND's Incomplete Adjuvant (AIF)

The immunogenic (humoral) activity of the E7 Δ21-26 preparation embedded in chitosan nanoparticles has been studied in 6 week old C57BL/6 (H-2$^b$) female mice purchased from Charles River, in the presence of AIF.

A. Material and Methods

At day 0, a group of 6 mice receives a 0.2 ml (50 μg) injection of an AIF emulsion in the presence of 1 μg murine GMC-SF and 1.5 μg murine IL-2 through intramuscular route. An AIF 5 μg booster injection is given at day 21 and day 60.

A blood sample is taken at the retro-orbital level from each mouse before the first injection at day −2 and 12 days after the last immunization.

- 6 control mice receive the same immunogen-free preparations.
- 3 mice receive 100 μg of the preparation and the absence of disease symptoms is studied during the 7 days following the injection.

The lack of toxicity in the preparation is measured by the absence of clinical signs: (behaviour, hairs, weight) and through anatomic study after necropsy.

B. Results

The mice immunized by the E7 Δ21-26 preparation embedded in chitosan nanoparticles in the presence of AIF do not show any clinical sign or anatomic injury.

None of the three mice immunized with 100 μg of the preparation shows any disease symptoms during the 7 days following the injection.

The immune response is measured by:

1. Humoral Response

The presence in the serum of IgG type antibodies directed against the native E7 recombinant protein, is measured by ELISA and expressed in titer (reverse of the dilution giving an optical density higher than 0.3).

FIG. 7

The mice immunized with the E7 Δ21-26 preparation embedded in chitosan nanoparticles in the presence of AIF have very high anti-E7 IgG type antibody titers.

The neutralizing activity of such antibodies is measured using the following immunosuppression test. A 1/50 dilution of the serum taken at day −2 and day 72 is incubated for 2 hours with 50 ng/ml of native E7. These dilutions are then applied on human macrophages, pretreated with IFN-γ for 16 hours. After 24 hours of culture, the culture supernatants are recovered and the produced TNF-α amount is measured by an ELISA test, the DTA50 DuoSet (R&D). The neutralizing serums prevent the E7 protein from inducing the expression of TNF-α, while the non neutralizing serums allow for the synthesis of this cytokine.

The results are given in neutralization %.

FIG. 8

The antibodies induced by the E7 Δ21-26 preparation embedded in chitosan nanoparticles in the presence of AIF have a very high neutralizing power.

EXAMPLE 2

Systemic and Mucosal Immune Response

Example 2.1

Immunogenic Activity of the E7 Δ21-26 Protein in the Presence of IMS 1113 (SEPPIC)

The immunogenic (humoral) activity of the E7 Δ21-26 preparation has been studied in 6 week old C57BL/6 (H-$2^b$) female mice purchased from Charles River, in the presence of IMS 1113 (SEPPIC).

A. Material and Methods

At day 0, a group of 6 mice receives a 0.2 ml injection containing 50 μg of E7 Δ21-26 in the presence of IMS 113 with 1 μg murine GM-CSF and 1.5 μg murine IL-2 through intramuscular route, as well as 20 μl containing 20 μg of the same preparation through intranasal route.

At days 7, 14 and 21, those mice receive through intranasal route 20 μl, i.e. 20 μg of the IMS 1113 preparation.

At day 60, those mice receive a 0.2 ml injection containing 5 μg of the IMS 1113 preparation and 20 μl containing 20 μg of the same preparation through intranasal route.

A blood sample is taken at the retro-orbital level as well as a vaginal secretion sample from each mouse before the first injection at day −2 and 12 days after the last immunization.

6 control mice receive the same immunogen-free preparations.

3 mice receive 100 μg of the preparation and the absence of disease symptoms is studied during the 7 days following the injection.

The lack of toxicity in the preparation is measured by the absence of clinical signs: (behaviour, hairs, weight) and through anatomic study after necropsy.

B. Results

The mice immunized by the E7 Δ21-26 preparation in the presence of IMS 1113 do not show any clinical sign and no anatomic injury.

None of the three mice immunized with 100 μg of the preparation shows any disease symptoms during the 7 days following the injection.

The immune response is measured by:

1. Humoral Response 1.1. Production of G Isotype Antibodies in the Serums

The presence in the serum of IgG type antibodies directed against the native E7 recombinant protein, is measured by ELISA and expressed in titer (reverse of the dilution giving an optical density higher than 0.3).

FIG. 9

The mice immunized with the E7 Δ21-26 preparation in the presence of IMS 1113 have very high anti-E7 IgG type antibody titers.

The neutralizing activity of such antibodies is measured using the following immunosuppression test. A 1/50 dilution of the serum taken at day −2 and day 72 is incubated for 2 hours with 50 ng/ml of native E7. These dilutions are then applied on human macrophages, pretreated with IFN-γ for 16 hours. After 24 hours of culture, the culture supernatants are recovered and the produced TNF-α amount is measured by an ELISA test, the DTA50 DuoSet (R&D). The neutralizing serums prevent the E7 protein from inducing the expression of α-TNF, while the non neutralizing serums allow for the synthesis of this cytokine.

The results are given in neutralization %.

FIG. 10

1.2. Production of Isotype A Antibodies in the Vaginal Secretions

The presence in the serum of IgA type antibodies directed against the native E7 recombinant protein, is measured by ELISA and expressed in titer (reverse of the dilution giving an optical density higher than 0.3).

FIG. 11

The mice immunized with the E7 Δ21-26 preparation in the presence of IMS 1113 have very high anti-E7 IgA type antibody titers.

Example 2.2

Immunogenic Activity of the E7 Δ21-26 Protein Embedded in Chitosan in the Presence of AIF (Systemic Route) or in the Presence of PBS (Nasal Route)

The immunogenic (humoral) activity of the E7 Δ21-26 preparation embedded in chitosan has been studied in 6 week old C57BL/6 (H-$2^b$) female mice, purchased from Charles River.

A. Material and Methods

At day 0, a group of 6 mice receives a 0.2 ml injection containing 50 μg of E7 Δ21-26 embedded in chitosan in the presence of AIF with 1 μg murine GM-CSF and 1.5 μg murine IL-2 through intramuscular route, as well as 20 μl containing 20 μg of the same preparation in the presence of PBS added with 1 μg murine GM-CSF and 1.5 μg murine IL-2 through intranasal route.

At days 7, 14 and 21, those mice receive through intranasal route 20 μl, i.e. 20 μg of E7 Δ21-26 embedded in chitosan in the presence of PBS.

At day 60, those mice receive a 0.2 ml injection containing 5 μg of the AIF preparation and 20 μl containing 20 μg of the same preparation in the presence of PBS through intranasal route.

A blood sample is taken at the retro-orbital level as well as a vaginal secretion sample from each mouse before the first injection at day −2 and 12 days after the last immunization.

6 control mice receive the same immunogen-free preparations.

3 mice receive 100 μg of the preparation and the absence of disease symptoms is studied during the 7 days following the injection.

The lack of toxicity in the preparation is measured by the absence of clinical signs: (behaviour, hairs, weight) and through anatomic study after necropsy.

B. Results

The mice immunized by the E7 Δ21-26 preparation embedded in chitosan do not show any clinical sign and no anatomic injury.

None of the three mice immunized with 100 μg of the preparation shows any disease symptoms during the 7 days following the injection.

The immune response is measured by:
1. Humoral Response
1.1. Production of G Isotype Antibodies in the Serums
The presence in the serum of IgG type antibodies directed against the native E7 recombinant protein, is measured by ELISA and expressed in titer (reverse of the dilution giving an optical density higher than 0.3).

FIG. 12

The mice immunized with the E7 Δ21-26 preparation embedded in chitosan have very high anti-E7 IgG type antibody titers.

The neutralizing activity of such antibodies is measured using the following immunosuppression test. A 1/50 dilution of the serum taken at day −2 and day 72 is incubated for 2 hours with 50 ng/ml of native E7. These dilutions are then applied on human macrophages, pretreated with IFN-γ for 16 hours. After 24 hours of culture, the culture supernatants are recovered and the produced α-TNF amount is measured by an ELISA test, the DTA50 DuoSet (R&D). The neutralizing serums prevent the E7 protein from inducing the expression of TNF-α, while the non neutralizing serums allow for the synthesis of this cytokine.

The results are given in neutralization %.

FIG. 13

1.2. Production of Isotype A Antibodies in the Vaginal Secretions
The presence in the serum of IgA type antibodies directed against the native E7 recombinant protein is measured by ELISA and expressed in titer (reverse of the dilution giving an optical density higher than 0.3).

FIG. 14

The mice immunized with the E7 Δ21-26 preparation embedded in chitosan have very high anti-E7 IgA type antibody titers.

EXAMPLE 3

Protective Anti-trumor Response

Example 3.1

The Injection of E7Δ21-26 Proteins in the Presence of ACF Followed by AIF Generates an Anti-tumor Resistance The measurement of a protective anti-tumor response in mice immunized with the E7 Δ21-26 preparation in the presence of ACF followed by AIF (example 1.1) has been tested as follows.

12 days after the last immunization, the mice were injected with 500,000 C3 cells, through subcutaneous route (s-c) in the flank. The C3 cells are embryo cells from C57BL/6 origin, transformed with the full HPV-16 genome and the ras oncogene. The tumor growth is evaluated once a week through measuring the tumor surface.

FIG. 15

A tumor has grown in all the control mice treated only with the adjuvant. Amongst the 6 mice immunized with the E7 Δ21-26 preparation in the presence of ACF followed by AIF:

4 mice did not grow any tumor,
in 1 mouse, a tumor grew and then stabilized,
in 1 mouse, a tumor grew.

The E7 Δ21-26 generates in mouse, in the presence of ACF and of AIF, a specific immune response specific against a tumor induced by the type 16 human Papillomavirus.

EXAMPLE 4

Therapeutic Anti-tumor Response

The ability of the E7Δ21-26 in the presence of AIF to induce the rejection of preimplanted C3 tumors has been tested in C57BL/6 (H-2b) mice as follows.

Example 4.1

Preparation of the Therapeutic Model

A. Material and Methods
Mice (groups of 8) were injected in s.c. into the flank with an increasing number of C3 cells: 0; $5.10^2$; $5.10^3$; $5.10^4$ and $5.10^5$. The tumor growth is evaluated once a week through measuring the tumor surface.

Results

TABLE I

Evaluation of the tumor growth through measuring the tumor surface*

| Number of injected cells | D0 | D12 | D17 | D24 | D31 |
|---|---|---|---|---|---|
| 0e + 0 | 0 | 0 | 0 | 0 | 0 |
| 5e + 2 | 0 | 0 | 0 | 0.1 | 1.9 |
| 5e + 3 | 0 | 0 | 0 | 0 | 2.8 |
| 5e + 4 | 0 | 0 | 0 | 10 | 6.9 |
| 5e + 5 | 0 | 25 | 202 | sacrificed | sacrificed |

*The surface, expressed in $mm^2$, represents the average obtained from measuring the surface of 8 tumors.

The mice, having received $5.10^5$ cells, have all grown a tumor 12 days after the cell injection (8/8).

Amongst the mice having received $5.10^4$ cells, 4 mice out of 8 grew a tumor 21 days after the cell injection and 4 mice out of 8, 28 days after the injection.

Amongst the mice having received $5.10^3$ cells, 1 mouse out of 8 grew a tumor 35 days after the cell injection and 3 mice out of 8, 42 to 60 days after the injection and the fourth other mice still did not show any tumor.

Amongst the mice having received $5.10^2$ cells, 1 mouse out of 8 grew a tumor 35 days after the cell injection, the other 7 mice still do not grow any tumor.

Example 4.2

Anti-tumor Response in the Mouse Having Received a $7.10^3$ and $9.10^3$ Dose of C3 Cells Expressing the E7 Protein A. Material and Methods
Mice were first injected in s.c. into the flank 7,000 or 9,000 C3 cells (day 0). On days 2, 9, 16 and 23, the mice received an intramuscular injection of 10 μg of the E7Δ21-26 preparation in AIF and 1 μg GM-CSF and murine IL2. On days 9, 16, 23 and 60, the mice received an intramuscular injection of 10 μg of the E7Δ21-26 preparation in AIF.

The size of the tumors was measured twice a week as described hereinabove in example 4.1.

B. Results

Figure 1:
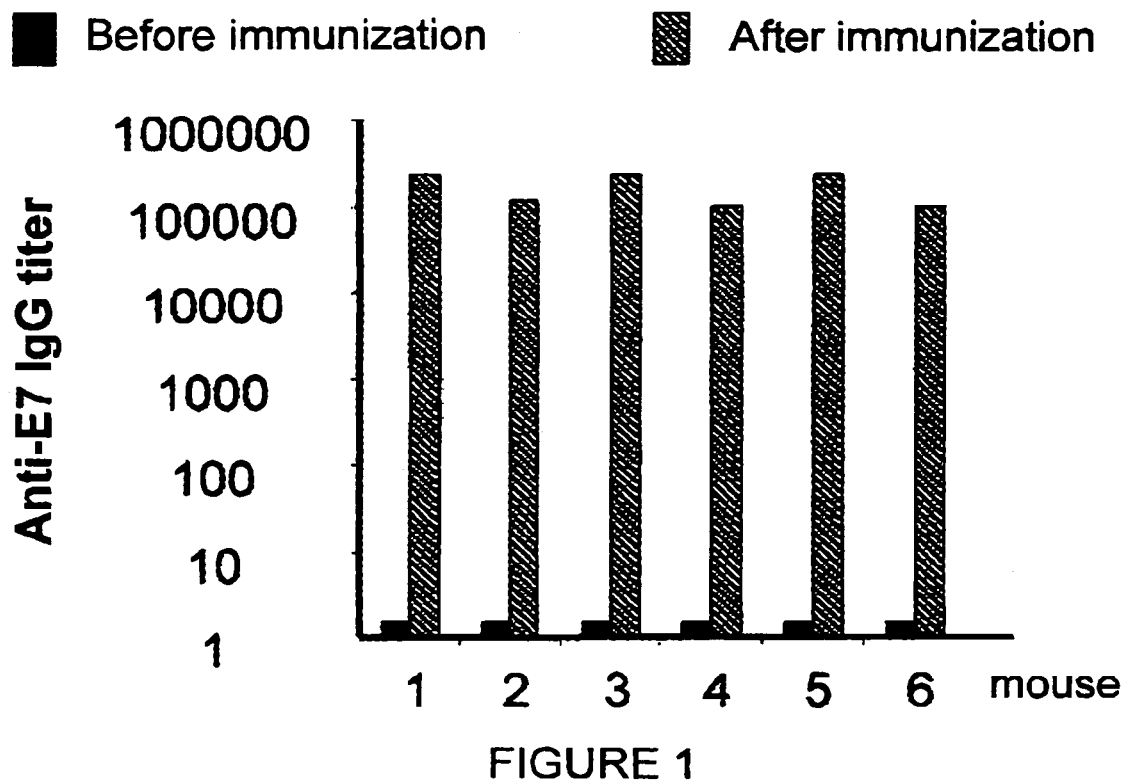
FIG. 1 is a graph of mouse serum anti-E7 IgG antibody titers, before and after immunization with an E7Δ21-26 preparation.
Figure 2:
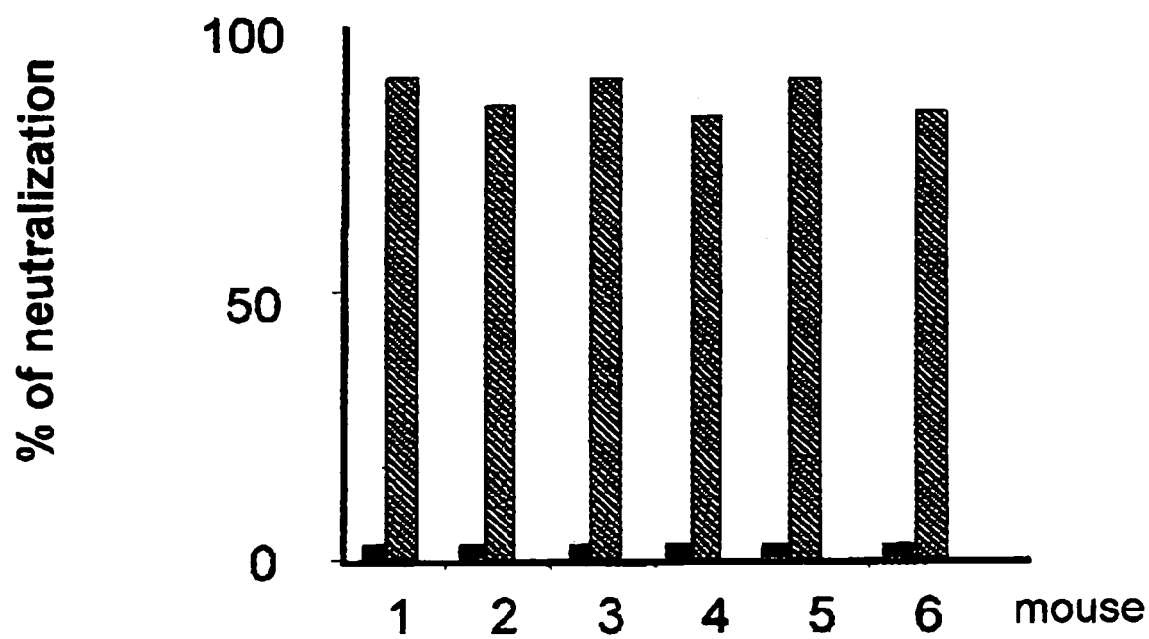
FIG. 2 is a graph of the neutralization percentage of mouse serum anti-E7 IgG antibodies, before and after immunization with an E7Δ21-26 preparation.
Figure 3:
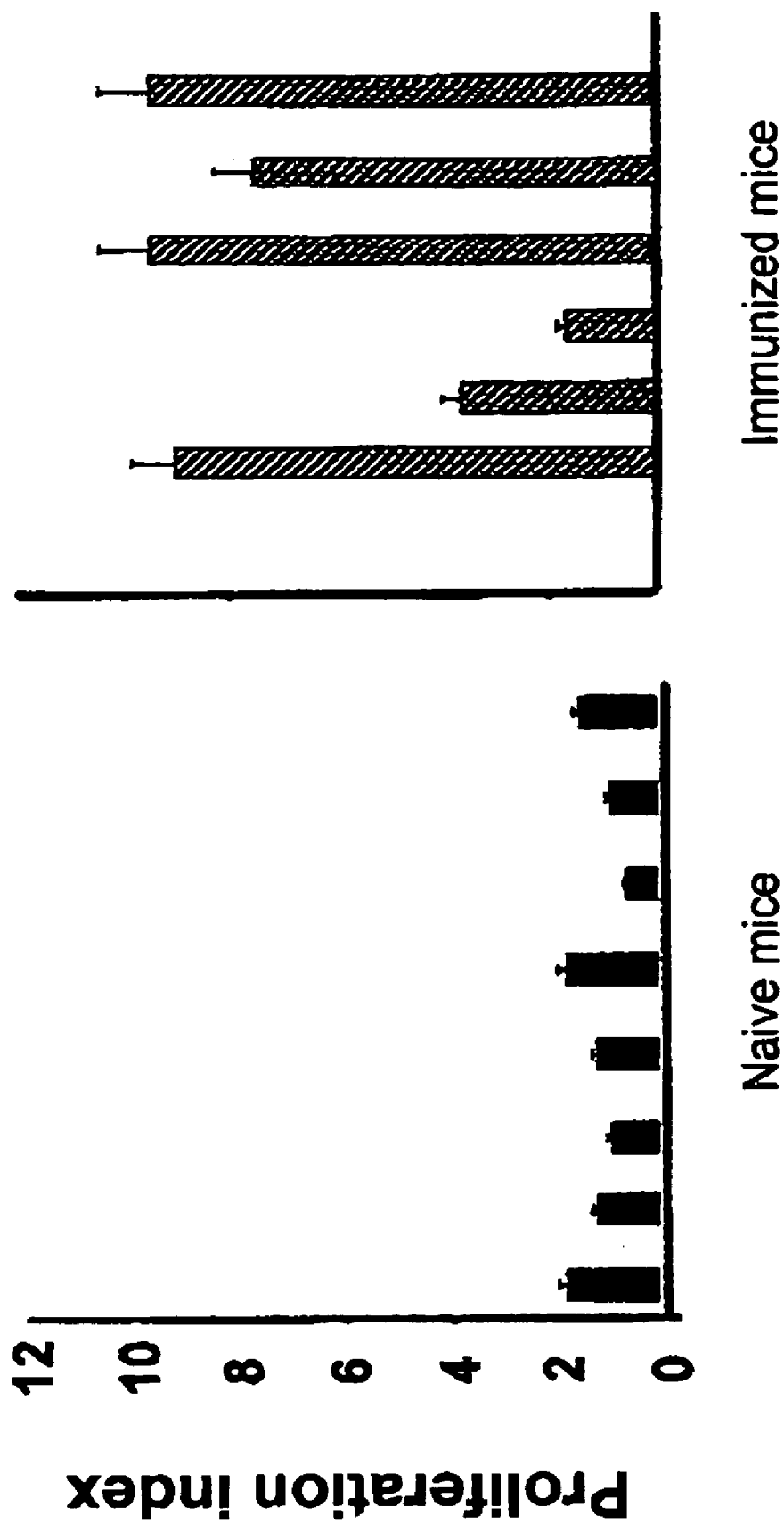
FIG. 3 is a graph of the splenocyte Ip proliferation index of naïve mice and mice immunized with an E7Δ21-26 preparation cultured in the presence of the native E7 protein.
Figure 4:
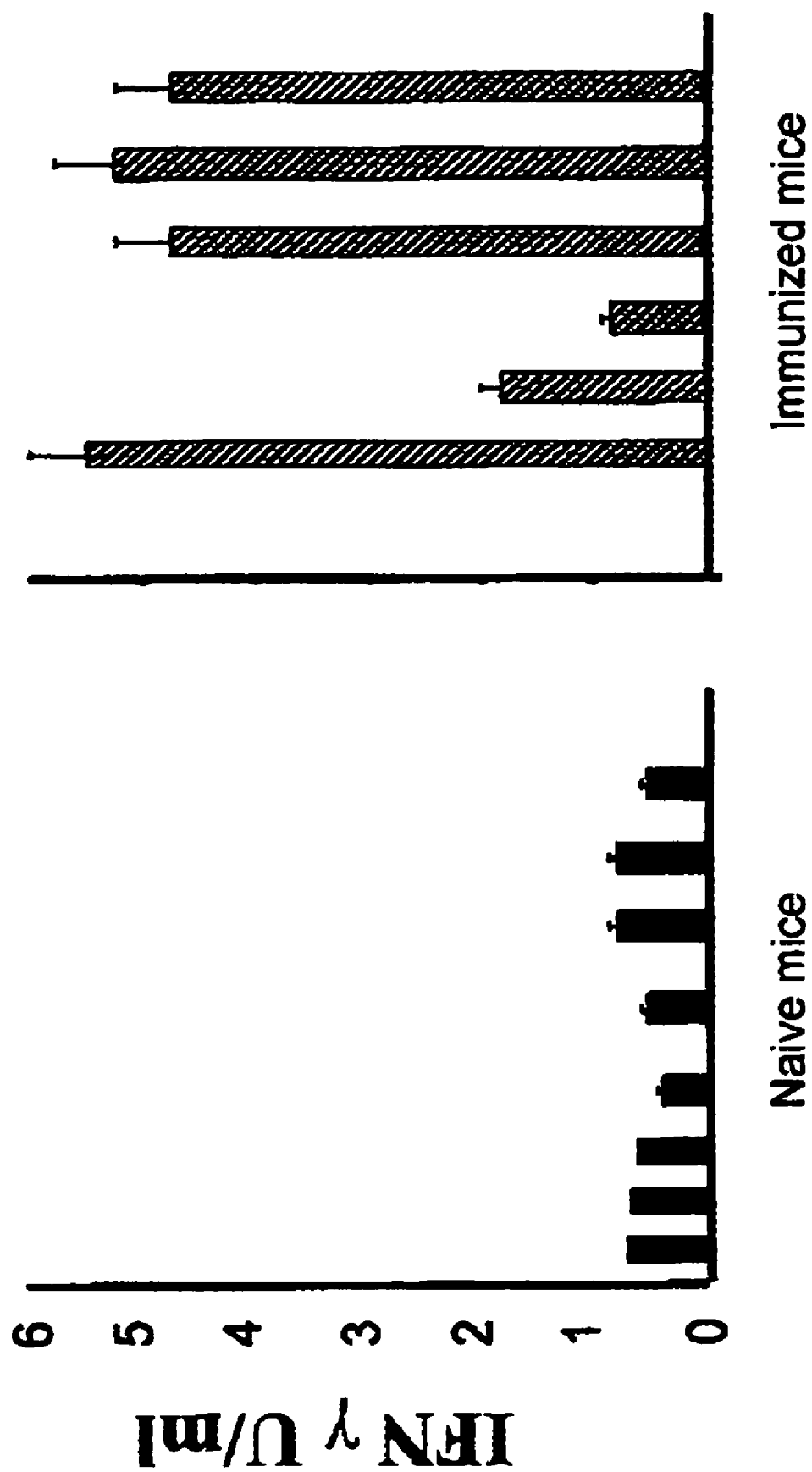
FIG. 4 is a graph of the splenocyte γ-IFN rate of naïve mice and mice immunized with an E7Δ21-26 preparation cultured in the presence of the native E7 protein.
Figure 5:
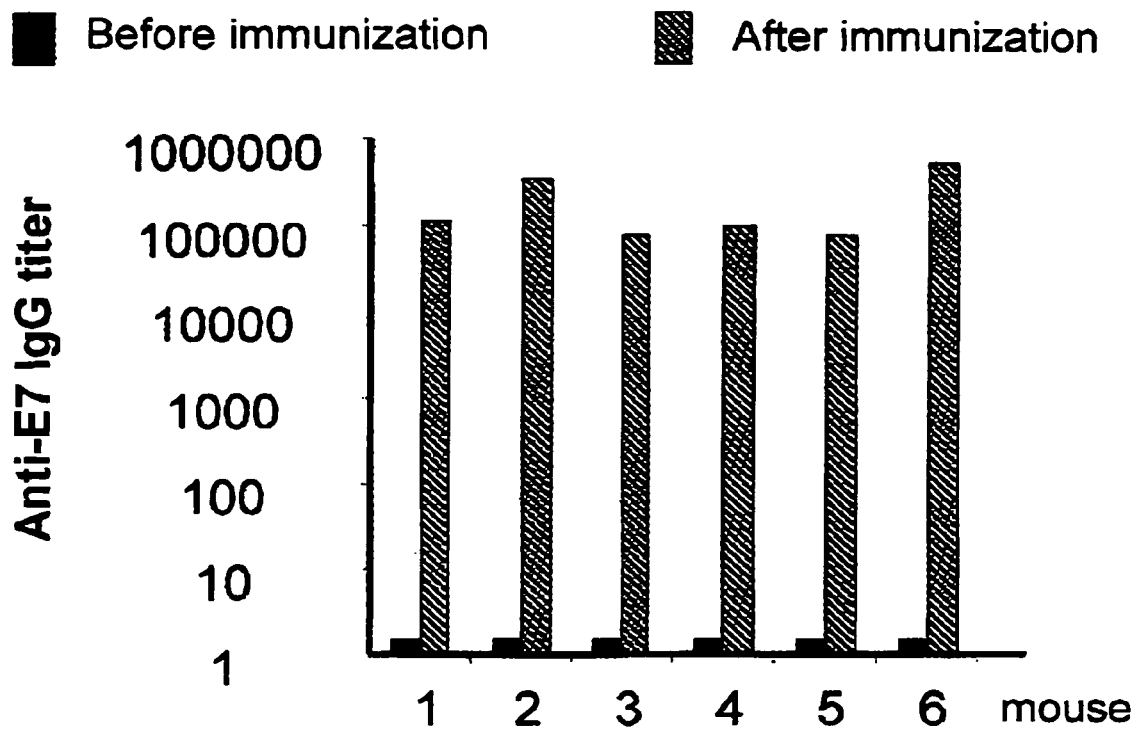
FIGS. 5 to 8 show graphs of mouse serum anti-E7 IgG titers and neutralization percentages of mouse serum anti-E7 IgG antibodies, before and after immunization with an E7Δ21-26 preparation.
Figure 6:
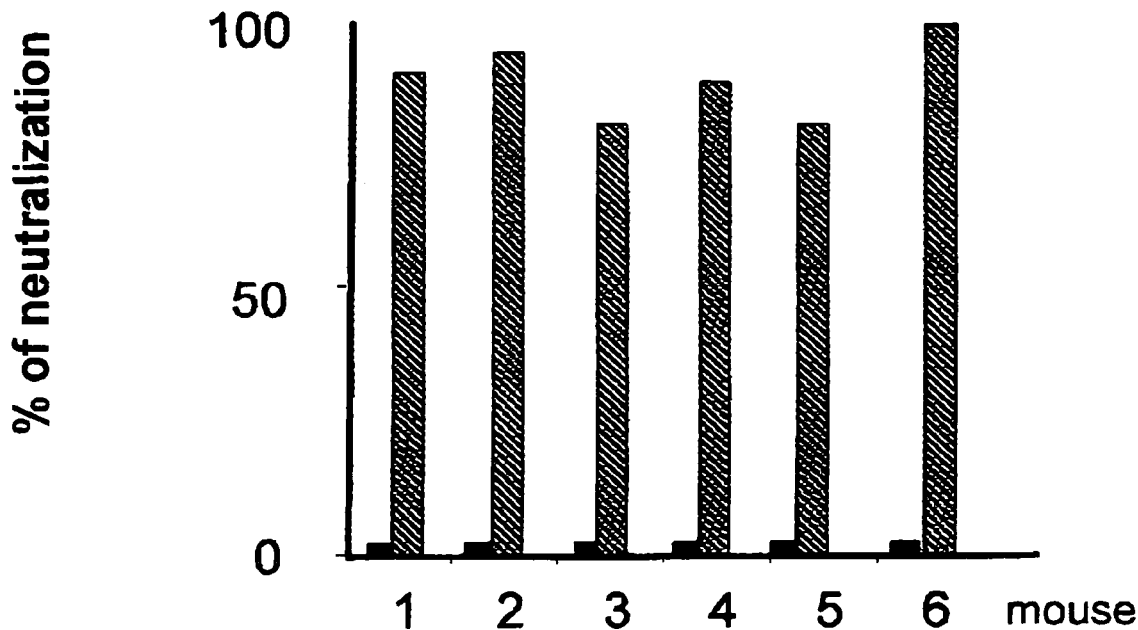
Figure 7:
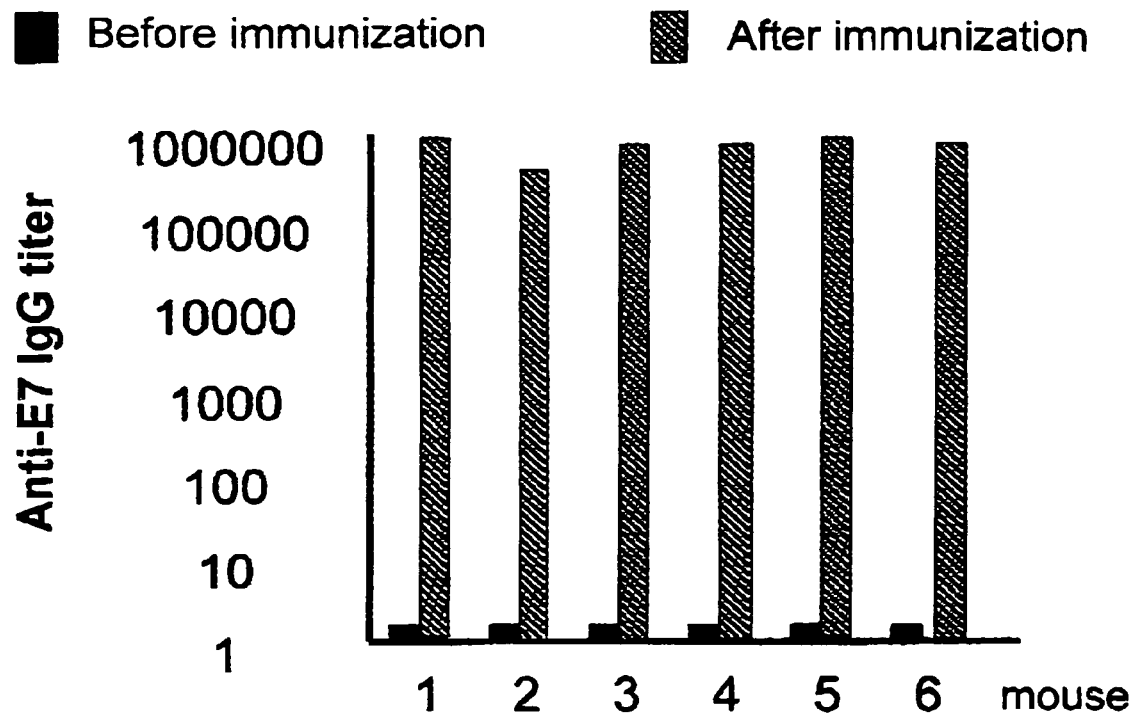
Figure 8:
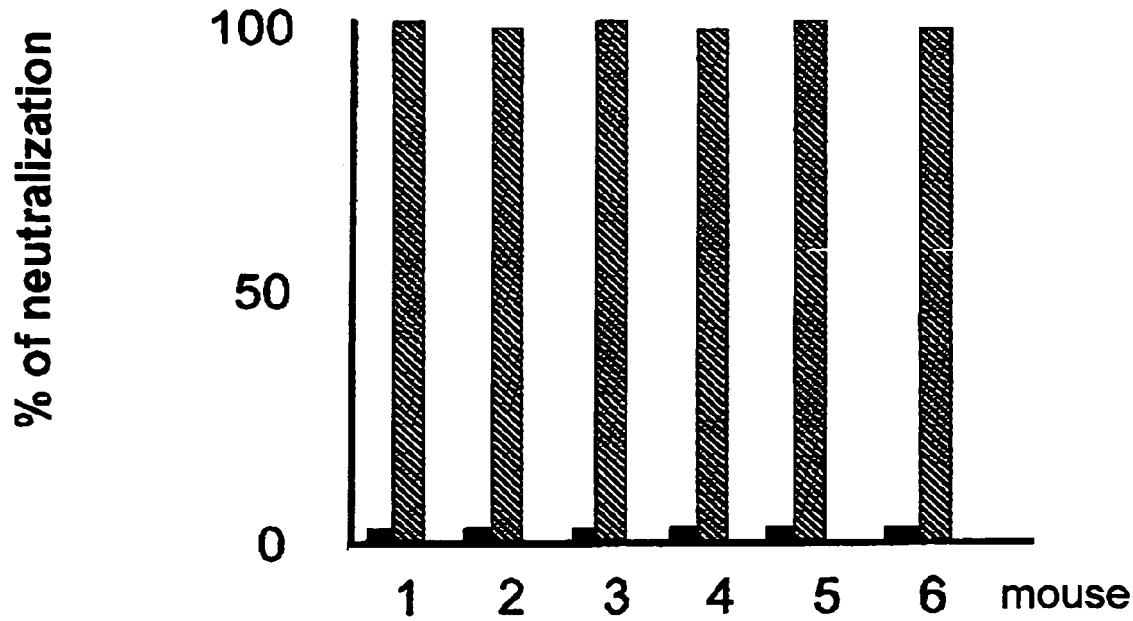
Figure 9:
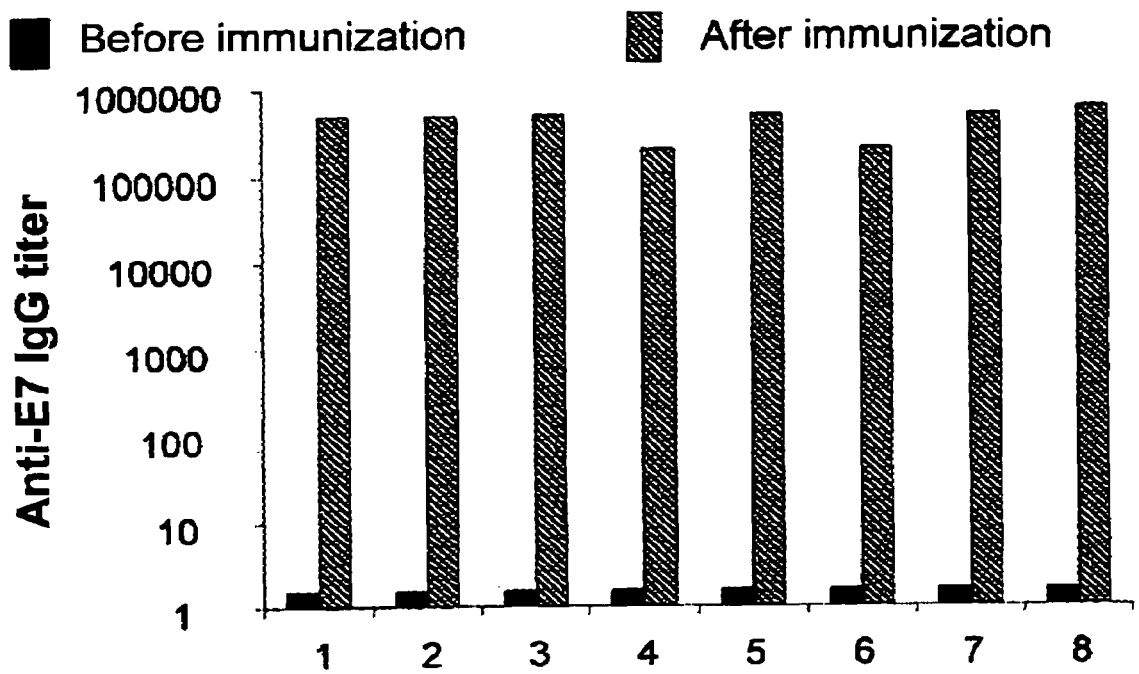
FIGS. 9 and 10 show graphs of mouse serum anti-E7 IgG titers and neutralization percentages of mouse serum anti-E7 IgG antibodies, before and after immunization with an E7Δ21-26 preparation.
Figure 10:
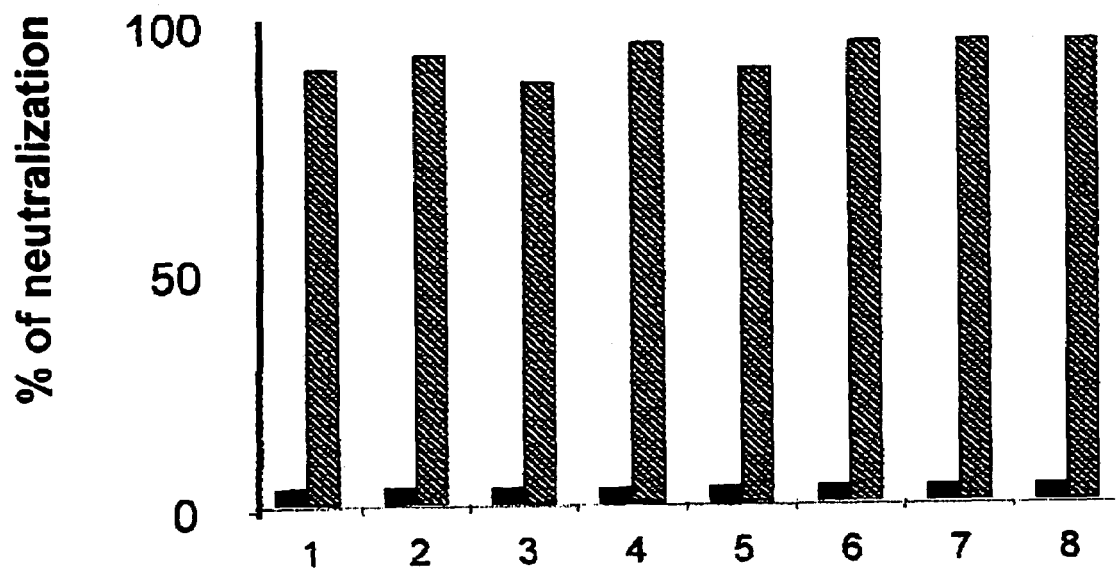
Figure 11:
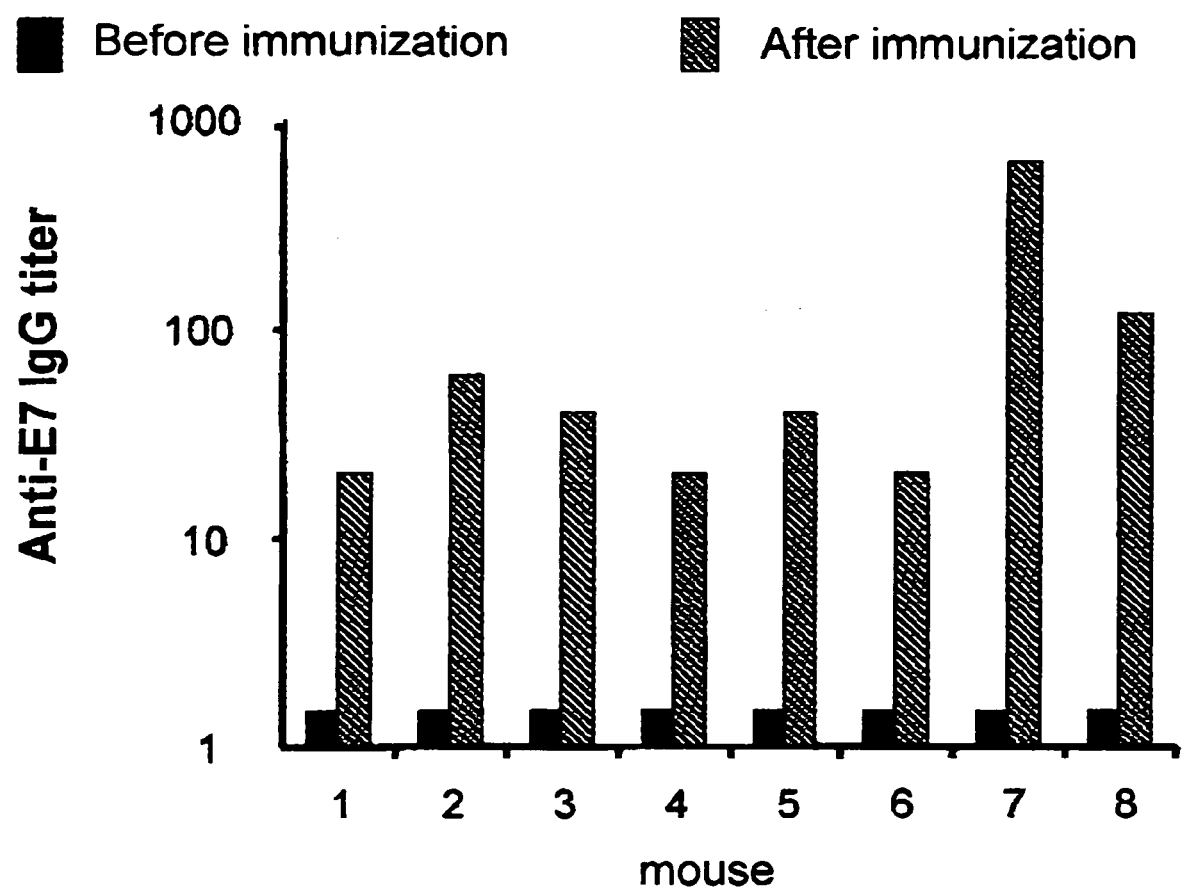
FIG. 11 is a graph showing the IgA rate present in mouse vaginal secretions, before and after immunization with an E7Δ21-26 preparation.
Figure 12:
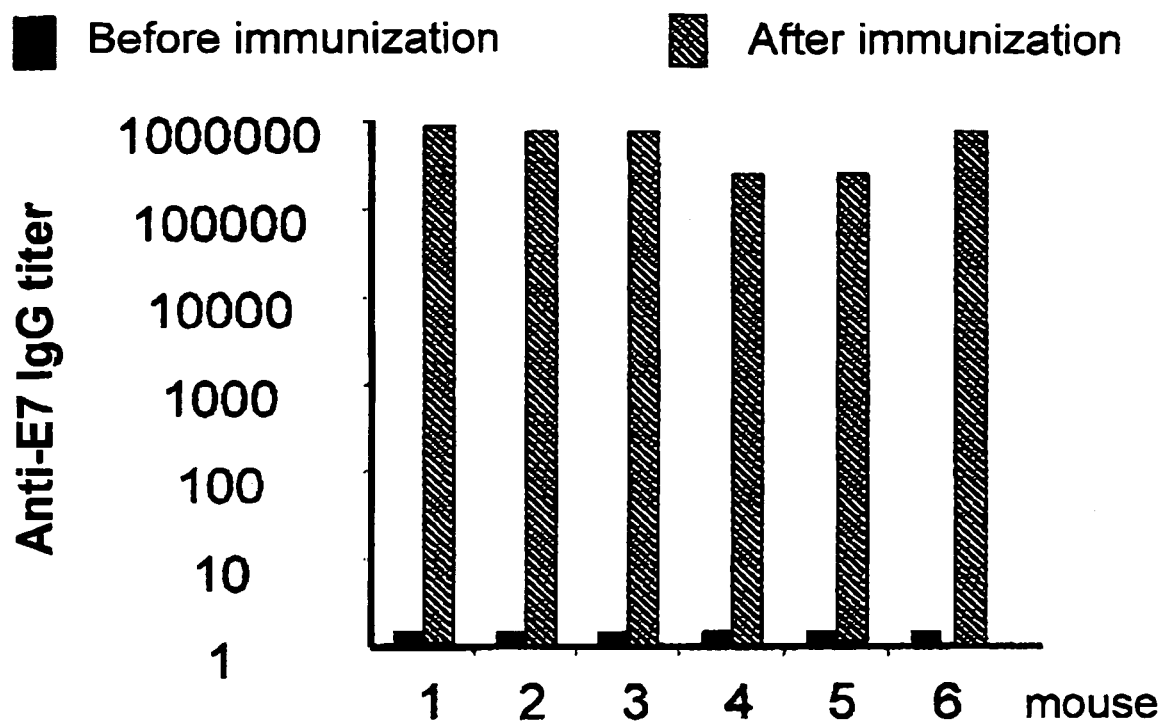
FIGS. 12 and 13 show graphs of the mouse serum anti-E7 IgG titer and neutralization percentages of mouse serum anti-E7 IgG antibodies, before and after immunization with an E7Δ21-26 preparation.
Figure 13:
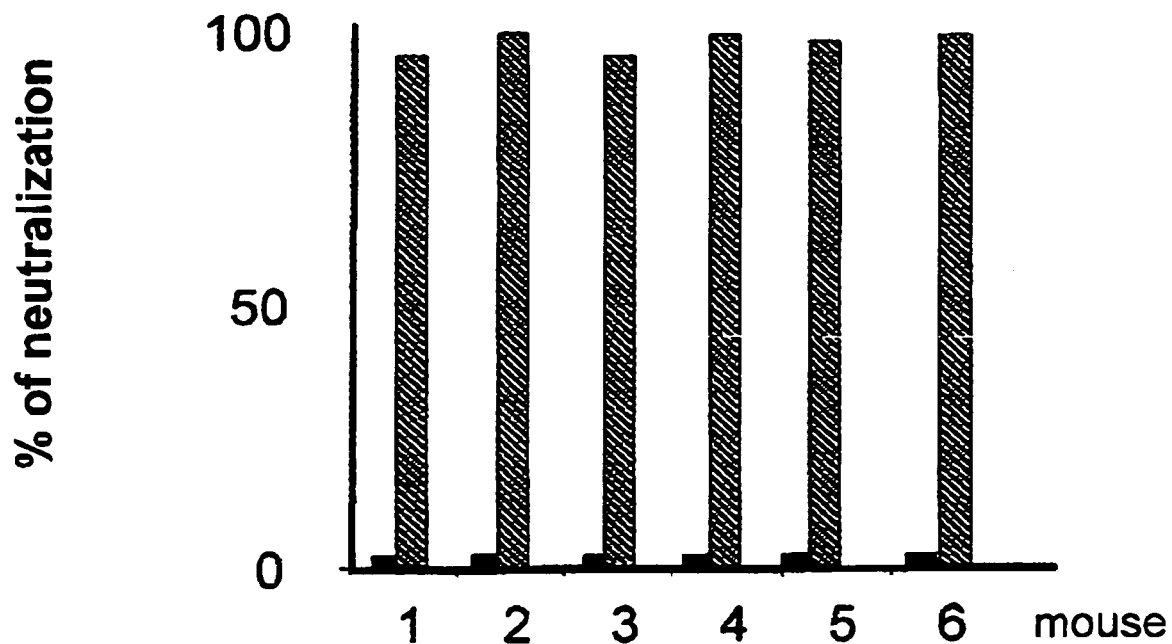
Figure 14:
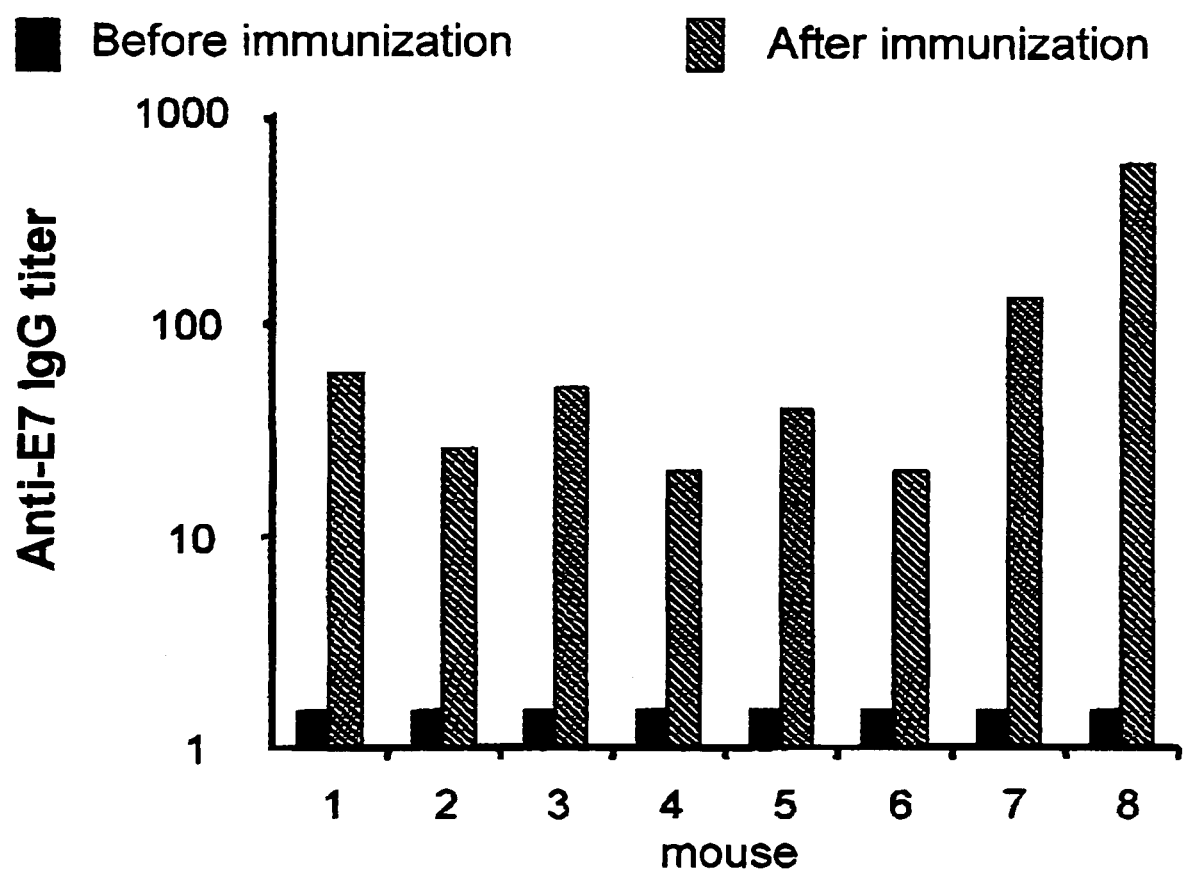
FIG. 14 is a graph showing the IgA rate present in mouse vaginal secretions, before and after immunization with an E7Δ21-26 preparation.
Figure 15:
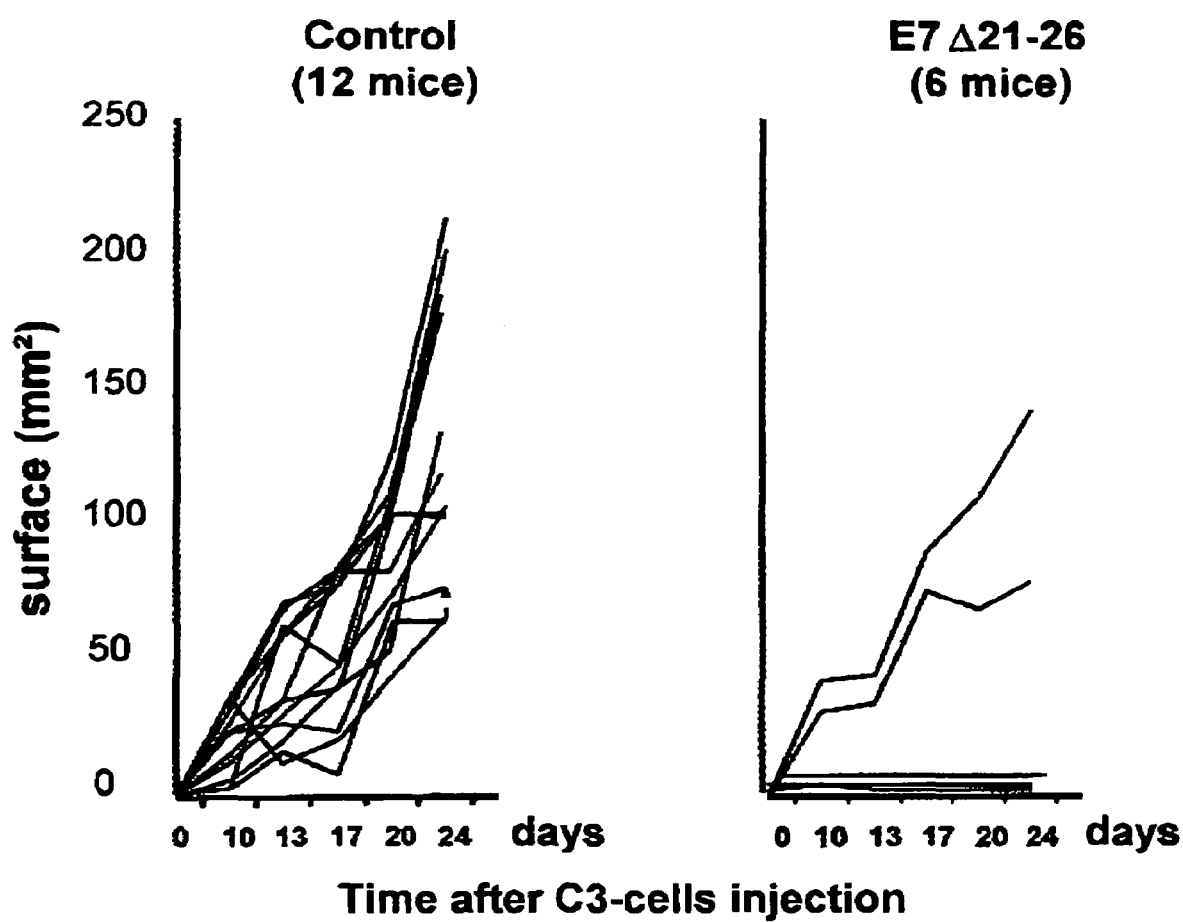
FIG. 15 is a graph showing the tumor growth of C3 cells injected to mice whether immunized or not with an E7Δ21-26 preparation.
Figure 16B:
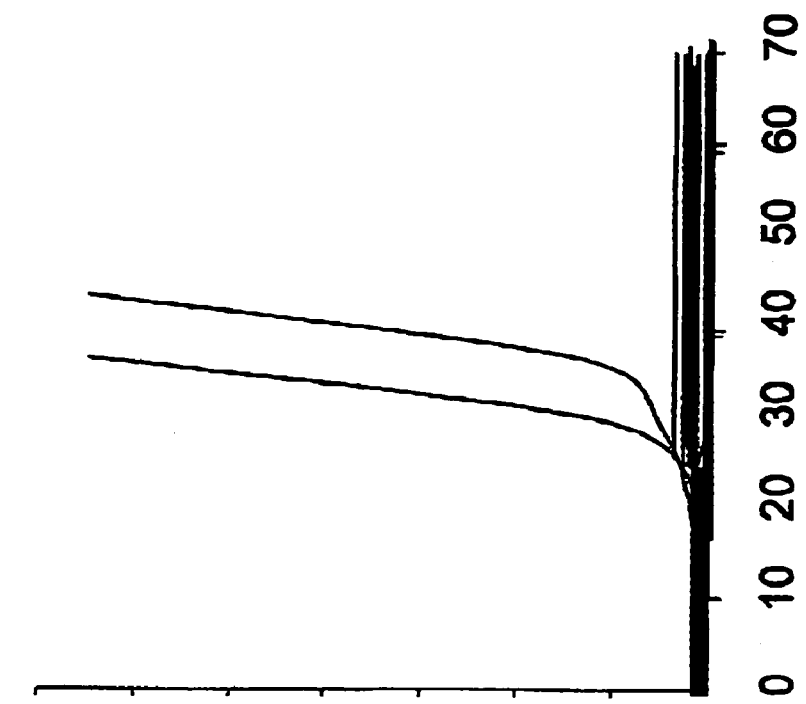
FIG. 16B represents mice treated with the E7Δ21-26; the abscissas represent the number of days after the injection of C3 cells; the ordinates, the tumor surface.
Figure 16A:
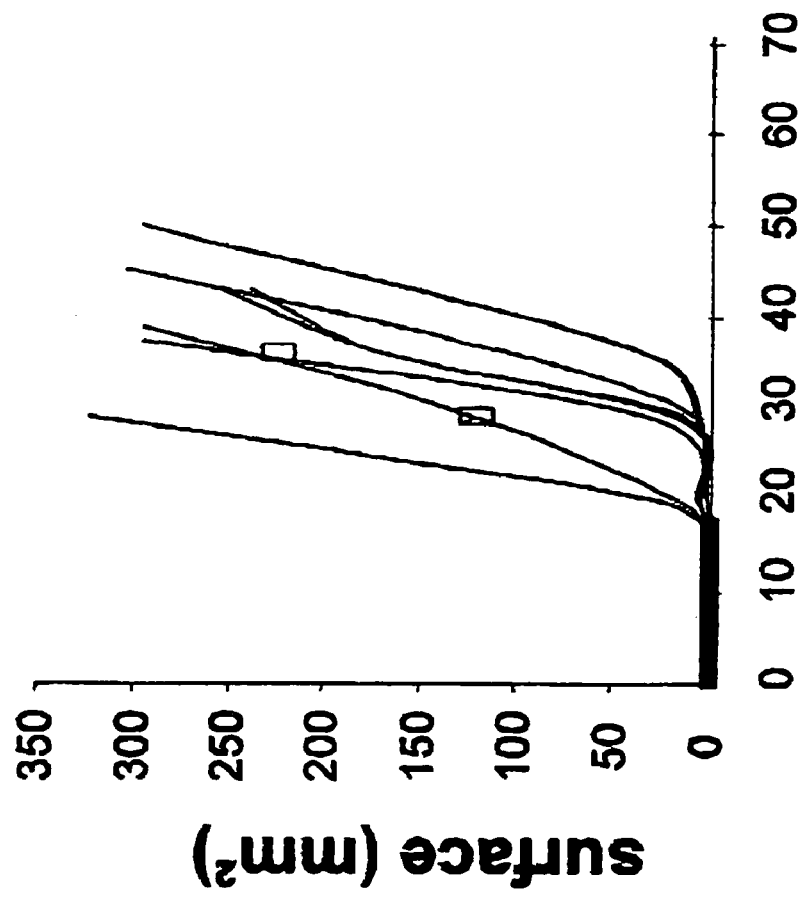

FIGS. 16 and 17 show the obtained results.

The control mice all grew tumors (8/8) 10 to 20 days after the injection of the C3 cells whereas 80% (7,000 injected cells—FIG. 16) and 75% (9,000 injected cells—FIG. 17) of the immunized mice did not grow any.

EXAMPLE 5

Stimulation of a Lymphocyte Mixed Reaction with Dendritic Cells Pretreated with the E7Δ21-26 Mutated E7 Protein A unidirectional autologous mixed lymphocyte reaction comprises co-culturing mononucleated cells of an individual (effector or responding cells) on its antigen carrying dendritic cells (stimulating cells). The effector cells having receptors specific for the antigen carried by the stimulating cells, proliferate. The proliferation is measured by the tritiated thymidine incorporation test.

The dendritic cells originate from the differentiation of monocytes obtained through elutriation from PBMCs from the peripheral blood of a donor (Sallusto et al., Journal of Experimental Medicine, 1994, 179, 1109-18). Monocytes, at $2.5.10^6$ cells/ml are cultured in teflon pouches in RPMI 1640 enriched with SAB (10%), GMC-SF (50 ng/ml) and IL4 (1,000 units/ml). After 6 days of culture, those cells show the phenotype of differentiated dendritic cells.

These thus obtained dendritic cells are then treated with a 3 μg/ml dose of native E7, or of E7 Δ21-26 and/or of the culture medium, then co-cultured in plates with round bottom 96 wells, with the PBMCs of the same donor in the ratios: 1/10; 3/10 and 10/10. 18 hours before the end of the reaction, 0.5 μCi of tritiated thymidine/well is added. The results, given in strokes per minute, are presented in FIG. 18.

When the dendritic cells are pre-incubated with the native E7 protein, then cultured with the responding cells, no proliferation is observed (because of the immunosuppressive activity of the native E7 protein). When the dendritic cells are pre-incubated with the mutated E7 protein (lacking the immunosuppressive activity of the native protein), a proliferation of the stimulating ones is observed.

EXAMPLE 6

Lack of Immunosuppressive Activity of the Mutated E7 Proteins

The lack of in vitro immunosuppressive activity has been measured using a cellular proliferation test. Mononucleated cells of human peripheral blood are isolated, then cultured in round bottom wells at a rate of 150,000 cells/well in the presence of 3 μg/ml of the different native E7 proteins and their respective mutant or in the presence of culture supernatant (SN) of E7 HPV 16 (Δ21-25) vaccine culture, a donation from MP Kieny, Transgene and in the presence of a booster antigen (PPD+TT). The cellular culture is continued at 37° C. in a wet atmosphere loaded with 5% $CO_2$ for 6 days. The cellular proliferation is measured by the tritiated thymidine incorporation test. The results, given in strokes per minute, are summarized in table II hereinafter.

TABLE II

| Control medium | 25,000 | 40,000 | 33,000 | 45,000 |
|---|---|---|---|---|
| PD1/3-HPV16-E7 | 5,000 | | | |
| PD1/3-HPV16-E7 mutant (C24G; E26Q) | 20,000 | | | |
| His-HPV16-E7 | | 10,000 | | |
| His-HPV16-E7 mutant (C24S; E26Q) | | 35,000 | | |
| His-HPV16-E7 | | | 7,500 | |
| His-HPV16-E7 mutant (Δ21-26) | | | 30,000 | |
| SN-Vaccinia E7 HPV 16 (Δ21-25 | | | | 40,000 |

The obtained results show that the mutants were detoxicated (loss of the immunosuppressive activity of the native protein).

REFERENCES

AUSUBEL F M, Brent R. Kingstone Re, Moore D D, Seidaman J G, Smith J A Struhl K editors, (1989), Current protocols in Molecular Biology, Wiley Interscience
AUCOUTURIER et al., 2001, Vaccine, 19: 2666-2672
BARAS et al., 1999, Infect. Immun., 67: 2643-2648
BASAK et al., 1995, J. Pept. Sci., 1(6): 383-395
CHEN et al., 1987, Mol. Cell. Biol. Vol. 7: 2745-2752
CRUZ, I. et al., 1999, Br. J. Cancer, vol. 81; 881-889
De SMEDT, T., B. Pajak, E. Muraille, L. Lespagnard, E. Heinen, P. De Baetselier, J. Urbain, O. Leo and M. Moser. 1996. Regulation of dendritic cell numbers and maturation by lipopolysaccharide in vivo. J. Exp. Med. 184: 1413-1424
EL SHERIF A M et al., 2001, J. Pathol, 195(2): 179-185
FRANKEL et al., 1988, Cell, vol. 55
FELTKAMP, M. C., H. L. Smits, M. P. Vierboom, R. P. Minnaar, B. M. de Jongh, J. W. Drijfhout, J. ter Schegget, C. J. Melief and W. M. Kast. 1993. Vaccination with cytotoxic T lymphocyte epitope-containing peptide protects against a tumor induced by human papillomavirus type 16-transformed cells. Eur. J. Immunol. 23:2242-2249
FRALEY 1980, J. Biol. Chem., vol. 255:10431
FLOTTE et al., 1992, Am. J. Respir. cell Mol. Biol., vol. 7: 349-356
GAIT (ed.), 1984, Nucleic acid hybridization
GERARD C M, 2001, Vaccine, vol. 19: 2583-2589
GIANNINI et al., 1998, Clin. EXP. Immunol, 113(2): 183-189
GIANNINI ET al., 2002, Int. J. CANCER, 97(5): 654-659
GOPAL 1985, Mol. Cell. Biol., vol. 5:1188-1190
GLOVER (ed.), 1985, DNA Cloning: A practical approach, vol. I and II. Oligonucleotide synthesis, MRL Press, Ltd, Oxford, U.K.
GRAHAM et al., 1973, Virology, vol. 52: 456-457
HOUBEN WEYL, 1974, In Methode der Organischen Chemie, E. Wunsch Ed., Volumes 15-I et 15-II, Thieme, Stuttgart
HUYGEN et al., 1996, Nature Medicine, vol. 2 (8):893-898
HARLAND et al., 1985, J. Cell. Biol. vol. 101:1094-1095
KIEFER H. et al., 1996, Biochemistry, vol. 35(50):16077-16084
MCLAUGHLIN B A et al., 1996, Am. J. Hum. Genet, vol. 59:561-569
MERRIFIELD R B, 1965a, Nature, vol. 207(996):522-523
MERRIFIELD, 1965b, Science, vol. 150(693):178-185
MUDERSPACH L. et al., 2000, Clinical Cancer Research, vol. 6: 3406-3416
NICOLAU et al., 1987, Methods enzymol., vol. 149:157-176
OSEN W et al., 2001, Vaccine, vol. 19: 4276-4286

POTTER et al., 1984, Proc. Natl. Acad. sci. USA, vol. 81 (22):7161-7165
TUCKER J., GRISSHAMMER R., Biochem J., 1996, vol., 317(Pt3):891-899
SAMBROOK J FRITSCH E F et MANIATIS T, 1989, Molecular Cloning: A Laboratory Manual, 2 ed. Cold Spring Harbor Laboratory, Cold Spring Harbor, N.Y.
SAMULSKI et al. 1989, J. Virol., vol. 63:3822-3828
SCHOELL W M J, 1999, Gynecologic Oncology, vol. 74: 448-455
SEEDORF K, 1985, Virology, vol. 145 (1):181-185
SKAUGRUD et al. 1999, Biotechnol. Genet. Eng. Rev., 16:23-40
TACSON et al., 1996, Nature Medicine, vol. 2 (8):888-892
TUR-KASPA, 1986, Mol. Cell. Biol., vol. 6:716-718

The invention claimed is:

1. A vaccine composition lacking a preventive or curative immunosuppressive property towards a cancer caused by a Papillomavirus infection, comprising, as the active ingredient, a non immunosuppressive mutated E7 protein, comprising the amino acid sequence consisting, from the N-terminal end to the C-terminal end, of:
   i. the 1-19 amino acid sequence of sequence SEQ ID No. 3;
   ii. an amino acid sequence possessing (a) the substitution of at least one amino acid, compared to the 20-29 corresponding amino acid sequence of sequence SEQ ID No. 3 or (b) the deletion of at least four consecutive amino acids, compared to the 20-29 corresponding amino acid sequence of sequence SEQ ID No. 3; and
   iii. the 30-98 amino acid sequence of sequence SEQ ID No. 3,
in association with one or more physiologically compatible immunity adjuvants.

2. A vaccine composition according to claim 1, wherein the mutated E7 protein is characterized in that the amino acid region (ii) of said mutated E7 protein comprises at least two substitutions of amino acids, compared to the corresponding 20-29 peptide region of amino acids of sequence SEQ ID No. 3 of the native protein.

3. A vaccine composition according to claim 2, wherein the mutated E7 protein is characterized in that the amino acid region (ii) of said mutated E7 protein comprises three, four, five, six, seven, eight, nine or ten substitutions of amino acids, compared to the corresponding 20-29 peptide region of amino acids of sequence SEQ ID No. 3 of the native protein.

4. A vaccine composition according to claim 2, wherein the mutated E7 protein is characterized in that the Cys residues in position 24 and Glu in position 26 have been substituted by a distinct amino acid residue.

5. A vaccine composition according to claim 4, wherein the mutated E7 protein is the (CYS24GLY, GLU26GLN) E7 protein.

6. A vaccine composition according to claim 4, wherein the mutated E7 protein is the (CYS24SER, GLU26GLN) E7 protein.

7. A vaccine composition according to claim 1, wherein the mutated E7 protein is characterized in that the amino acid region (ii) of said mutated E7 protein comprises the deletion of five, six, seven, eight, nine or ten consecutive amino acids, compared to the corresponding 20-29 amino acid sequence of SEQ ID No. 3.

8. A vaccine composition according to claim 7, wherein the mutated E7 protein is characterized in that the amino acid region (ii) of said mutated E7 protein comprises the deletion of six consecutive amino acids, compared to the corresponding 20-29 amino acid sequence of SEQ ID No. 3.

9. A vaccine composition according to claim 8, wherein the mutated E7 protein consists in the mutated E7 protein having the amino acid sequence comprising the deletion of the corresponding amino acids 21 to 26 of the SEQ ID No. 3 sequence of the native E7 protein.

10. A vaccine composition according to claim 7, wherein the mutated E7 protein is characterized in that the amino acid region (ii) of said mutated E7 protein comprises the deletion of five consecutive amino acids, compared to the corresponding 20-29 amino acid sequence of SEQ ID No. 3.

11. A vaccine composition according to claim 10, wherein the mutated E7 protein consists in the mutated E7 protein having the amino acid sequence comprising the deletion of the corresponding amino acids 21 to 25 of the SEQ ID No. 3 sequence of the native E7 protein.

12. A vaccine composition according to claim 1, characterized in that it comprises at least one adjuvant able to preferably orient the immune response towards the production of antibodies neutralizing the immunosuppressive activity of the native E7 protein.

13. A vaccine composition according to claim 12, characterized in that it comprises at least one adjuvant able to preferably orient the immune response towards the production of IgA isotype antibodies.

14. A vaccine composition according to claim 12, characterized in that it comprises at least one adjuvant able to preferably orient the immune response towards the production of IgG isotype antibodies.

15. A vaccine composition according to claim 12, characterized in that it comprises the combination (i) of one adjuvant able to preferably orient the immune response towards the production of IgA isotype antibodies and (ii) of one adjuvant able to preferably orient the immune response towards the production of IgG isotype antibodies.

16. A vaccine composition according to claim 15, characterized in that it comprises at least one immunity adjuvant able to induce a humoral and cellular immune response.

17. A vaccine composition according to claim 7, characterized in that the cellular response is further characterized by the proliferation of lymphocytes expressing the CD8 antigen and specifically recognizing the wild E7 protein.

18. An immunogenic composition inducing an immune response towards the HPV-16 Papillomavirus native E7 protein, without simultaneously inducing an immunosuppression, said composition comprising, as the active ingredient, a non immunosuppressive mutated E7 protein, comprising the amino acid sequence consisting, from the N-terminal end to the C-terminal end, of:
  i. the 1-19 amino acid sequence of sequence SEQ ID No. 3;
  ii. an amino acid sequence possessing (a) the substitution of at least one amino acid, compared to the 20-29 corresponding amino acid sequence of sequence SEQ ID No. 3 or (b) the deletion of at least four consecutive amino acids, compared to the 20-29 corresponding amino acid sequence of sequence SEQ ID No. 3; and
  iii. the 30-98 amino acid sequence of sequence SEQ ID No. 3, in association with one or more physiologically compatible excipients or immunity adjuvants.

19. A preventive or curative vaccine composition for a cancer caused by a HPV-16 infection, characterized in that it comprises an immunologically efficient amount of a nucleic acid encoding a mutated E7 protein as defined in one of claim 1, an expression cassette comprising said nucleic acid or a recombinant vector comprising said expression cassette.

20. Purified neutralizing antibodies directed against the expression product of the DNA encoding the mutated E7 protein such as defined according to one of claim 1.

21. Purified neutralizing A composition for passive vaccination towards a HPV-16 infection containing antibodies according to claim 20.

22. A vaccine composition lacking any preventive or curative immunosuppressive property towards a cancer caused by a Papillomavirus infection, characterized in that it comprises, as the active ingredient, an appropriate amount of autologous or allogenic dendritic cells towards the individual to be treated, said autologous dendritic cells having been incubated with a mutated E7 protein such as defined in one of claim 1 and thereby made able to present said mutated E7 protein to T cells.

23. A method of preventing or treating some cancers associated with an infection through the HPV-16 type Papillomavirus which comprises inoculating a subject prone to or afflicted with such a cancer a vaccine composition according to claim 1.

24. A method for preparing a pharmaceutical composition for preventing or treating cancers associated with an infection through the HPV-16 type Papillomavirus, comprising a step of combining a mutated E7 protein as defined in claim 1 with one or more physiologically compatible immunity adjuvant.

* * * * *